US009637902B2

(12) United States Patent
Burt et al.

(10) Patent No.: US 9,637,902 B2
(45) Date of Patent: May 2, 2017

(54) SELF-ADHESIVE LAVATORY TREATMENT COMPOSITIONS

(71) Applicant: Reckitt Benckiser LLC, Parsippany, NJ (US)

(72) Inventors: Diane Joyce Burt, Montvale, NJ (US); Priscila Mira Luciano, Montvale, NJ (US)

(73) Assignee: Reckitt Benckiser LLC, Parsippany, NJ (US)

( * ) Notice: Subject to any disclaimer, the term of this patent is extended or adjusted under 35 U.S.C. 154(b) by 0 days.

(21) Appl. No.: 14/309,986

(22) Filed: Jun. 20, 2014

(65) Prior Publication Data

US 2014/0298577 A1    Oct. 9, 2014

Related U.S. Application Data

(63) Continuation-in-part of application No. PCT/GB2013/051882, filed on Jul. 15, 2013.

(Continued)

(51) Int. Cl.
*C11D 3/43* (2006.01)
*E03D 9/03* (2006.01)
*A61L 9/04* (2006.01)
*A61L 9/05* (2006.01)
*C11D 17/04* (2006.01)
(Continued)

(52) U.S. Cl.
CPC .............. *E03D 9/032* (2013.01); *A61L 9/048* (2013.01); *A61L 9/05* (2013.01); *C11D 1/58* (2013.01); *C11D 1/835* (2013.01); *C11D 1/86* (2013.01); *C11D 3/2065* (2013.01); *C11D 3/2068* (2013.01); *C11D 3/43* (2013.01); *C11D 17/003* (2013.01); *C11D 17/0056* (2013.01); *C11D 17/044* (2013.01); *E03D 9/005* (2013.01); *E03D 9/022* (2013.01); *C11D 1/29* (2013.01);
(Continued)

(58) Field of Classification Search
None
See application file for complete search history.

(56) References Cited

U.S. PATENT DOCUMENTS 6,881,710 B1 *   4/2005   O'Lenick et al. ............ 510/123
2004/0147422 A1   7/2004   Hatch et al.
(Continued)

FOREIGN PATENT DOCUMENTS

WO    2009105233 A1    8/2009
WO    2011158029 A1   12/2011

OTHER PUBLICATIONS

Notification of Transmittal of the International Search Report and the Written Opinion of the International Searching Authority for PCT/GB2013/051882 dated Oct. 8, 2013.
(Continued)

*Primary Examiner* — Necholus Ogden, Jr.
(74) *Attorney, Agent, or Firm* — Norris McLaughlin & Marcus PA

(57) ABSTRACT

Self-adhesive lavatory treatment compositions comprise an adhesion promoter based on a fatty alcohol polyglycol ether as may be represented by the following structural formula (I):

$$R\text{—}O\text{—}(CH_2\text{—}CH_2\text{—}O)_n H \qquad (I)$$

within which, R is an $C_{12}$-$C_{24}$ aliphatic mono- or polyalkene moiety, and n has a value of from 1 to 50, an organic solvent constituent, a surfactant, and water.

17 Claims, 2 Drawing Sheets

Related U.S. Application Data

(60) Provisional application No. 61/672,029, filed on Jul. 16, 2012, provisional application No. 61/683,879, filed on Aug. 16, 2012, provisional application No. 61/724,758, filed on Nov. 9, 2012.

(51) Int. Cl.
| | | |
|---|---|---|
| *E03D 9/00* | (2006.01) | |
| *E03D 9/02* | (2006.01) | |
| *C11D 1/835* | (2006.01) | |
| *C11D 1/86* | (2006.01) | |
| *C11D 17/00* | (2006.01) | |
| *C11D 1/58* | (2006.01) | |
| *C11D 3/20* | (2006.01) | |
| *C11D 1/72* | (2006.01) | |
| *C11D 1/29* | (2006.01) | |
| *C11D 1/62* | (2006.01) | |

(52) U.S. Cl.
CPC .................. *C11D 1/62* (2013.01); *C11D 1/72* (2013.01); *E03D 2009/024* (2013.01); *E03D 2009/026* (2013.01)

(56) References Cited

U.S. PATENT DOCUMENTS

| | | | |
|---|---|---|---|
| 2006/0040847 A1* | 2/2006 | Weibel | C11D 3/24 510/504 |
| 2006/0100128 A1* | 5/2006 | McCue | C11D 1/83 510/506 |
| 2006/0111265 A1* | 5/2006 | Rypkema | C11D 1/835 510/504 |
| 2008/0227682 A1* | 9/2008 | Chi-Cheng Feng | C11D 1/83 510/414 |
| 2008/0255017 A1 | 10/2008 | Dettinger et al. | |
| 2009/0215661 A1* | 8/2009 | Klinkhammer | C11D 3/18 510/192 |
| 2009/0305927 A1* | 12/2009 | Binns | C11D 3/3746 510/100 |

OTHER PUBLICATIONS

International Search Report for PCT/GB2013/0511882 dated Oct. 8, 2013.
Written Opinion of the International Searching Authority for PCT/GB2013/0511882 dated Oct. 8, 2013.

\* cited by examiner

SELF-ADHESIVE LAVATORY TREATMENT COMPOSITIONS

This is an application filed under 35 USC 371 of PCT/GB2013/051882, filed on 15 Jul. 2013, which claims priority to U.S. Ser. No. 61/672,029 filed 16 Jul. 2012, and U.S. Ser. No. 61/724,758 filed on 9 Nov. 2012.

The present invention relates to self-adhesive lavatory treatment compositions which are adapted to be directly adhered to a part of a lavatory appliance, e.g., the inner sidewall of a toilet bowl.

An adhesive lavatory composition known to the art is that described in U.S. Pat. No. 6,667,286. Therein is disclosed a sanitary agent for direct application to a sanitary object to be cleaned comprising: an adhesion promoter selected from the group consisting of long and long-chained organic molecules, which are at least partly hydrophilic, and the hydrophilic part of the adhesion promoter interacts at least in part with the water molecules in the presence of water and becomes "sticky" which enables said agent to adhere to said sanitary object even after a large number of rinse actions; water; anionic and/or nonionic and/or amphoteric surfactants ("tensides"); and optional components selected from the group consisting of fragrances, thickeners, colorants, preservatives, and combinations thereof; wherein the viscosity of the agent is at least 15,000 mPas. That document recites that "The agent can be 'sticky' either through a certain water content already in the formulation to be applied or the adhesion can be obtained by a light dampening of the surface—for example, by activating the flush water—and then applying the agent. Clearly while the compositions disclosed in U.S. Pat. No. 6,667,286 provide satisfactory performance characteristics, it is also clear that the sanitary agents necessarily require water in order to "become sticky" and thereby provide adhesion between the sanitary agent and a toilet bowl. A further review of this document reveals that the example compositions disclosed therein comprise 3-60% wt. of water as a necessary constituent.

Certain adhesive lavatory compositions are disclosed in EP 1978080 A1. The compositions disclosed therein necessarily comprise at least 20% wt., preferably at least 30% wt. of an adhesion promoter constituent, but are anhydrous compositions.

Further adhesive lavatory treatment compositions are known from US 2009/0325839, which compositions are disclosed as having a first surfactant constituent in amount of at least 7.5% wt., and additionally a blend of linear primary alcohols or a blend of ethoxylated linear primary alcohols, which compositions also necessarily exhibit a specified minimum "transport rate factor".

Thus while the prior art proposes certain compositions which exhibit satisfactory performance under certain conditions, there remains a real and continued need in the art for further improved lavatory treatment compositions which overcome shortcomings of prior art compositions.

The compositions of the self-adhesive lavatory treatment compositions address and overcome shortcomings of prior art lavatory treatment composition. These and further objects of the present invention will become apparent from a review of the following specification. Further, the compositions of the present invention exhibit excellent surface adhesion to dry surfaces, particularly to dry surfaces of lavatory appliances, e.g., toilets, bidets, urinals and the like, especially the inner sidewall of a toilet bowl.

Figure 1:
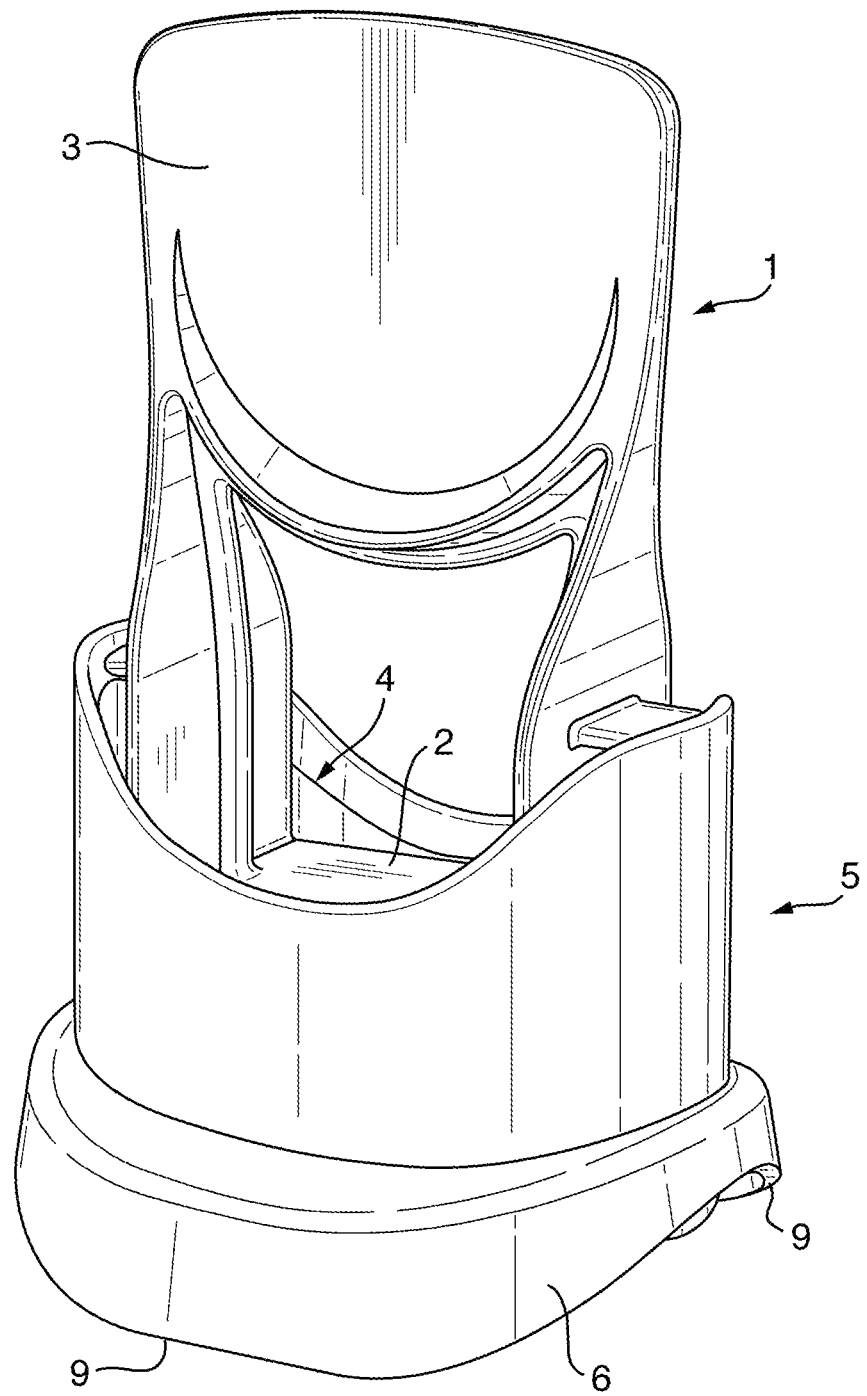
FIG. 1 illustrates a preferred dispenser for storing and dispensing a self-adhesive lavatory treatment composition according to the invention.

In one aspect the present invention is directed to a self-adhesive lavatory treatment composition which comprises (or, consists essentially of, or consists of):

up to 50% wt. of an adhesion promoter constituent based on a fatty alcohol polyglycol ether as may be represented by the following structural formula (I):

within which, R is an $C_{12}$-$C_{24}$ aliphatic mono- or poly-alkene moiety, and n has a value of from 1 to 50:

0.01-25% wt. of an organic solvent constituent, which is liquid at room temperature (20° C.);

0.1-25% wt. of a detersive surfactant constituent;

optionally a co-adhesion promoter constituent, preferably based on one or more oxyalkylenated compounds;

further optionally one or more further optional constituents which may impart a further aesthetic or technical benefit to the said self-adhesive lavatory treatment compositions; and, to 100% wt. of water;

wherein in use, the said self-adhesive lavatory treatment compositions may be applied and adhered to a dry or wetted ceramic surface, especially the interior sidewall in a toilet bowl or other lavatory appliance, and wherein the said self-adhesive lavatory treatment compositions is retained adhered to the said surface following a plurality of flushes of water impinging upon the adhered self-adhesive lavatory treatment compositions.

In a further aspect of the invention, there is provided a self-adhesive lavatory treatment composition as described above which comprises at least two different adhesion promoters, each based on a fatty alcohol polyglycol ether as may be represented by the following structural formula (I):

within which, R is an $C_{12}$-$C_{24}$ aliphatic mono- or poly-alkene moiety, and n has a value of from 1 to 50.

In a further aspect of the invention, there is provided a self-adhesive lavatory treatment composition as described above which comprises at least one cationic surfactant as the detersive surfactant constituent.

In a further aspect the present invention provides methods for the manufacture of the self-adhesive lavatory treatment compositions disclosed herein, as well as to methods for the use the disclosed self-adhesive lavatory treatment compositions in the treatment of lavatory appliances, and especially toilet bowls.

In a still further aspect of the invention there is provided a dispensing device, which comprises a quantity or mass of the self-adhesive lavatory treatment compositions disclosed herein.

Further features and aspects of the present invention will become more apparent from a further reading of the present specification.

A first essential constituent of the invention is at least one adhesion promoter based on a fatty alcohol polyglycol ether, as may be represented by the following structural formula (I):

within which:

R is an $C_{12}$-$C_{24}$ aliphatic mono- or poly-alkene moiety, and n has a value of from 1 to 50, but preferably n has a value of from 5 to 40, and most preferably has a value of from 25 to 35, inclusive.

Such a mono-alkene moieties includes only a single unsaturation between two adjacent carbon atoms, while a poly-alkene moiety includes at least two unsaturations between an appropriate number of carbon atoms in the R residue. Preferably R is a residue of a $C_{12}$-$C_{24}$ fatty alcohol having only one unsaturated bond between adjacent carbon atoms, viz., monounsaturation, although the residue of a $C_{12}$-$C_{24}$ fatty alcohol may also be polyunsaturated, having at least two unsaturated bonds between adjacent carbon atoms in the $C_{12}$-$C_{24}$ fatty alcohol residue. While R may have one or more branches, it is preferably linear. Mixtures or blends of two or more R residues, especially where such R residues are based on $C_{12}$-$C_{24}$ fatty alcohols may also be used.

In preferred embodiments the adhesion promoter based on a fatty alcohol glycol ether, conforms to the foregoing structural formula and comprises one or more unsaturations within the midsection of the R moiety, which is preferably a $C_{12}$-$C_{24}$ fatty alcohol, e.g, wherein the location of the at least one unsaturation (preferably a single unsaturation is present) is within the interior portion of the carbon molecules as measured from the midpoint of the $C_{12}$-$C_{24}$ aliphatic mono- or poly-alkene moiety and extending outwardly therefrom from both sides from the central carbon(s) which is/are equidistant from the two most distal carbon atoms of the longest carbon chain in the $C_{12}$-$C_{24}$ aliphatic mono- or poly-alkene moiety. Thus for example, if the R is a linear $C_{14}$ fatty alcohol, which is an even numbered fatty alcohol, then the central carbon(s) are the $C_7$ and $C_8$ carbons which are also at the midpoint as measured from the distal, $C_1$ and $C_{14}$ carbons of this fatty alcohol. Where, for example R is an odd numbered fatty alcohol, e.g. where R is a $C_{15}$ fatty alcohol, then the central carbon is the $C_8$ alcohol which is at the midpoint, as being equidistant from both the $C_1$ and $C_{15}$ carbons of the fatty alcohol. The midpoint carbon(s) may also be identified by the following equation:

$$N/2 = \text{midpoint carbon(s)}$$

wherein:

N is the number of carbon atoms in the longest carbon chain in the $C_{12}$-$C_{24}$ aliphatic mono- or poly-alkene moiety, corresponding to R in the foregoing structural formula. Wherein "N" is an even number then the foregoing equation will yield a value with no decimal remainder (e.g., for a $C_{14}$ aliphatic mono- or poly-alkene moiety, N=14, and thus N/2=7), then the midpoint carbons are the N/2 carbon, and the adjacent (N/2)+1 carbon. Such corresponds to the $7^{th}$ and $8^{th}$ carbons in the $C_{14}$ aliphatic mono- or poly-alkene moiety. Wherein "N" is an odd number then the foregoing equation will yield a value with a "0.5" decimal remainder, (e.g., for a $C_{15}$ aliphatic mono- or poly-alkene moiety, N=15, and thus N/2=7.5), then the midpoint carbons is (N/2)+0.5 carbon. Such corresponds to the $8^{th}$ carbon atom in the $C_{15}$ aliphatic mono- or poly-alkene moiety.

Preferably the one or more unsaturations present with the $C_{12}$-$C_{24}$ aliphatic mono- or poly-alkane moiety are between adjacent carbon atoms which are between the (N−N+2) carbon atoms and the (N−2) carbon atoms, and in order of increasing preference are: between the (N−N+4) carbon atoms and the (N−4) carbon atoms, and between the (N−N+5) carbon atoms and the (N−5) carbon atoms of the $C_{12}$-$C_{24}$ aliphatic mono- or poly-alkene moiety.

Preferably the one or more unsaturations present with the $C_{12}$-$C_{24}$ aliphatic mono- or poly-alkene moiety are between adjacent carbons which are within four carbons adjacent to one or both of the midpoint carbon(s), preferably are within three carbons adjacent to the one or both of the midpoint carbon(s), and especially preferably is/are between adjacent carbon atoms at least one of which is the midpoint carbon(s) in the longest carbon chain in the $C_{12}$-$C_{24}$ aliphatic mono- or poly-alkene moiety.

Particularly preferred fatty alcohol glycol ethers of the foregoing structural formula (I) include those which have two or less unsaturations in the R residue, and particularly preferred are those which have a single unsaturation in the R residue.

In certain preferred embodiments the R residue of the fatty alcohol polyglycol ether of the foregoing structural formula (I) is derived from a monounsaturated fatty alcohol which may be represented by the following formula (II):

$$CH_3(CH_2)_xCH=CH(CH_2)_y-CH_2OH \quad (II)$$

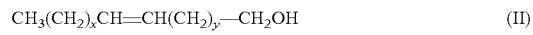

in which each of x and y are integers which have a value in the range of 6-32, preferably in the range of 8-18, and further preferably are within the respective ratios of from 0.5:1-1:0.5 preferably 0.75:1-1:0.75, and especially preferably about 1:1. Such is a monounsaturated alcohol. Preferably the fatty alcohol of the R residue is based on oleyl alcohol, preferably a monounsaturated oleyl alcohol.

Preferred fatty alcohol glycol ethers of the foregoing structural formula (I) include those which are presently commercially available in the Genapol® "O" series of nonionic surfactants which include:

Genapol O 020 oleyl alcohol polyglycol ether (2 EO)

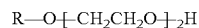
R—O—[—CH$_2$CH$_2$O—]$_2$H

Genapol O 050 oleyl alcohol polyglycol ether (5 EO)

R—O—[—CH$_2$CH$_2$—]$_5$H

Genapol O 080 oleyl alcohol polyglycol ether (8 EO)

R—O—[—CH$_2$CH$_2$O—]$_8$H

Genapol O 100 oleyl alcohol polyglycol ether (10 EO)

R—O—[—CH$_2$CH$_2$O—]$_{10}$H

Genapol O 109 oleyl alcohol polyglycol ether (10 EO)

R—O—[—CH$_2$CH$_2$O—]$_{10}$H

Genapol O 120 oleyl alcohol polyglycol ether (12 EO)

R—O—[—CH$_2$CH$_2$O—]$_{12}$H

Genapol O 150 oleyl alcohol polyglycol ether (15 EO)

R—O—[—CH$_2$CH$_2$O—]$_{15}$H

Genapol O 200 oleyl alcohol polyglycol ether (20 EO)

R—O—[—ECH$_2$CH$_2$O—]$_{20}$H

Genapol O 230 oleyl alcohol polyglycol ether (23 EO)

R—O—[—CH$_2$CH$_2$O—]$_{23}$H

Genapol O 300 oleyl alcohol polyglycol ether (30 EO)

R—O—[—CH$_2$CH$_2$O—]$_{30}$H and in the foregoing, R is a monounsaturated oleyl alcohol, and wherein a monounsaturation is at or near the midpoint from the terminal ends of the oleyl alcohol.

A particularly preferred R residue is based on oleyl alcohol which has a structure: $CH_3(CH)_7$—CH=CH—$(CH_2)_8$—OH, and contains a single monounsaturation at or near the midpoint from the terminal ends of the fatty alcohol.

Further preferred fatty alcohol glycol ethers of the foregoing structural formula (I) include those which are presently commercially available in the Genapol® "U" series of nonionic surfactants as well. Nonlimiting examples of such include: Genapol® 100 described to be a $C_{14/16/18}$ alkyl ethoxylate with 10 EO, $C_{14/16/18}$ alcohol, unsaturated, and Genapol® U 200 described to be a $C_{14/16/18}$ alkyl ethoxylate with 20 EO, $C_{14/16/18}$ alcohol, unsaturated.

Advantageously the adhesion promoter based on a fatty alcohol polyglycol ether is present in the compositions in amount of from about 50% wt. to about 50% wt., preferably from about 20% wt. to about 45% wt. based on the total weight of the self-adhesive lavatory treatment compositions of which they form a part. The identity of especially preferred adhesion promoters and their content within self-adhesive lavatory treatment compositions of the invention are disclosed with reference to one or more of the example compositions.

A next essential constituent of the invention is an organic solvent constituent which is liquid at room temperature (20° C.). The organic solvent constituent compositions comprise one or more organic solvents as the organic solvent constituent, but in preferred embodiments is a single organic solvent. By way of non-limiting example exemplary useful organic solvents which are liquid at room temperature (20° C.) and which may be included in the inventive compositions are those which are at least partially water-miscible such as alcohols (e.g., low molecular weight alcohols, such as, for example, ethanol, propanol, isopropanol, and the like), glycols (such as, for example, ethylene glycol, propylene glycol, hexylene glycol, and the like), water-miscible ethers (e.g. diethylene glycol diethylether, diethylene glycol dimethylether, propylene glycol dimethylether), water-miscible glycol ether (e.g. propylene glycol monomethylether, propylene glycol mono ethylether, propylene glycol monopropylether, propylene glycol monobutylether, ethylene glycol monobutylether, dipropylene glycol monomethylether, diethyleneglycol monobutylether), lower esters of monoalkylethers of ethylene glycol or propylene glycol (e.g. propylene glycol monomethyl ether acetate), and mixtures thereof. Glycol ethers having the general structure $R_a$—$R_b$—OH, wherein $R_a$ is an alkoxy of 1 to 20 carbon atoms, or aryloxy of at least 6 carbon atoms, and $R_b$ is an ether condensate of propylene glycol and/or ethylene glycol having from one to ten glycol monomer units.

Polyhydroxy organic solvents, viz, those having two or more —OH moieties are in certain cases, preferred for use.

The organic solvent may also be one or more further liquids such as glycerine and paraffin oil, as well as petroleum distillates and/or petroleum products, paraffinic oils usually based on n-alkanes, naphthenic oils usually based on cycloalkanes, aromatic oils such as those based on aromatic hydrocarbons, mineral oil, as well as technical grade mixtures of hydrocarbons may be used as or in the organic solvent. Examples of the latter include paraffinic hydrocarbons including both linear and branched paraffinic hydrocarbons; the former are commercially available as NORPAR solvents (ex. ExxonMobil Corp.) while the latter are available as ISOPAR solvents (ex. ExxonMobil Corp.) Mixtures of branched hydrocarbons especially as isoparaffins form are also contemplated to be useful.

In certain preferred embodiments the organic solvent constituent necessarily comprises (or consists essentially of, or consists of) at least one glycol or glycol ether, and further includes one or both of glycerine and/or mineral oil. When such at least one glycol or glycol ether is present in conjunction with one or both of glycerine and/or mineral oil, preferably the mass of the at least one glycol or glycol ether is at least about three times, preferably at least about four times that of the total mass of the glycerine and/or a mineral oil present.

In other preferred embodiments the organic solvent constituent necessary comprises (or consists essentially of, or consists of) glycerine and mineral oil, and further preferably the mass of the glycerine is at least about least about three times, preferably at least about four times that of the total mass of the mineral oil present.

In certain preferred embodiments the organic solvent constituent consists essentially of, yet more preferably consists of, at least one polyhydroxy organic solvents, e.g, a glycol or glycol ether, and further includes one or both of glycerine and/or mineral oil.

In further, certain preferred embodiments the organic solvent constituent consists essentially of, yet more preferably consists of, at least one glycol or glycol ether, and mineral oil.

In further, certain preferred embodiments the organic solvent constituent consists essentially of, yet more preferably consists of, at least one glycol or glycol ether, and both glycerine and mineral oil.

In further, certain preferred embodiments the organic solvent constituent consists essentially of, yet more preferably consists of, glycerine and mineral oil.

The organic solvent constituent comprises 1-25% wt. of the inventive compositions. Preferably, in order of increasing preference, the organic solvent constituent is present in an amount of at least about 0.01%, 0.1%, 0.5%, 0.75%, 1%, 1.25%, 1.5%, 1.75%, 2%, 2.25%, 2.5%, 2.75%, 3%, 3.25%, 3.5%, 3.75%, 4%, 4.25%, 4.5%, 4.75%, 5%, 5.25%, 5.5%, 5.75%, 6, 6.25% 6%, 6.5%, 6.75%, 7%, 7.25%, 7.5%, 7.75%, 8%, 8.25%, 8.5%, 8.75%, and 9% wt. of the inventive composition of which they form a part. Preferably, in order of increasing preference, the organic solvent constituent comprises not more than about 25%, 20%, 18%, 17%, 16%, 15%, 14.5%, 14%, 13.5%, 13%, 12.5%, 12%, 11.5%, 11%, 10.75%, 10.5%, 10.25%, 10%, 9.75%, 9.5%, 9.25%, 9%, 8.75%, 8.5%, 8.25%, 8%, 7.75%, 7.5%, 7.25%, 7%, 6.75%, 6.5%, 6.25%, 6%, 5.75%, 5.5%, 5.25%, 5%, 4.75%, 4.5%, 4.25%, 4%, 3.75%, 3.5%, 3.25%, 3%, 275% 2.5%, 2.25%, 2%, 1.75%, 1.5%, 1.25% and 1% wt. of the inventive composition of which they form a part. Particularly preferred amounts of the organic solvent constituent are recited in one or more of the Examples, with preferred ranges of the organic solvent constituent also disclosed in the Examples.

In certain preferred embodiments:

(a) the ratio (in % wt.) of polyhydroxy organic solvent: other solvents of the organic solvent constituent is in the range of about 4-12:1, preferably about 4.5-10:1, and especially preferably 4.5-8.5:1; and/or, (b) the ratio (in % wt.) of polyhydroxy organic solvent: mineral oil is in the range of about 5-20:1, more preferably about 7:18:1; and/or, (c) the ratios (in % wt.) of water:organic solvent constituent is in the range of about 5-20:1, more preferably about 6-16:1; and/or, (d) the ratios (in % wt.) of water:polyhydroxy organic solvent constituent is in the range of about 5-25:1, preferably about 7-25:1.

Particular and preferred specific ratios of (a), (b), (c) and or (d) are disclosed with reference to one or more of the examples.

In certain particularly preferred embodiments of the inventive compositions, the conditions outlined of at least two of, preferably at least three of, and particularly preferably the conditions outlined in all four of (a), (b), (c) and (d) are met/satisfied.

A next essential constituent is at least one detersive surfactant constituent. As the detersive surfactant constituent may be used one or more anionic, cationic, nonionic, amphoteric or zwitterionic surfactant compounds. Especially preferred surfactants of the surfactant constituent are disclosed with reference to the examples.

Exemplary useful anionic surfactants include the water-soluble salts, particularly the alkali metal, ammonium and alkylolammonium (e.g., monoethanolammonium or triethanolammonium) salts, of organic sulfuric reaction products having in their molecular structure an alkyl group containing from about 10 to about 20 carbon atoms and a sulfonic acid or sulfuric acid ester group. (Included in the term "alkyl" is the alkyl portion of aryl groups.) Examples of this group of synthetic surfactants are the alkyl sulfates, especially those obtained by sulfating the higher alcohols ($C_8$-$C_{18}$ carbon atoms) such as those produced by reducing the glycerides of tallow or coconut oil; and the alkylbenzene sulfonates in which the alkyl group contains from about 9 to about 15 carbon atoms, in straight chain or branched chain. Exemplary useful are linear straight chain alkylbenzene sulfonates in which the average number of carbon atoms in the alkyl group is from about 11 to 14.

Other exemplary useful anionic surfactants herein are the water soluble salts of: paraffin sulfonates containing from about 8 to about 24 (preferably about 12 to 18) carbon atoms; alkyl glyceryl ether sulfonates, especially those ethers of $C_8$-$C_{18}$ alcohols (e.g., those derived from tallow and coconut oil); alkyl phenol ethylene oxide ether sulfates containing from about 1 to about 4 units of ethylene oxide per molecule and from about 8 to about 12 carbon atoms in the alkyl group; and alkyl ethylene oxide ether sulfates containing about 1 to about 4 units of ethylene oxide per molecule and from about 10 to about 20 carbon atoms in the alkyl group.

Other useful anionic surfactants herein include the water soluble salts of esters of α-sulfonated fatty acids containing from about 0 to 20 carbon atoms in the fatty acid group and from about 1 to 10 carbon atoms in the ester group; water soluble salts of 2-acyloxy-alkane-1-sulfonic acids containing from about 2 to 9 carbon atoms in the acyl group and from about 9 to about 23 carbon atoms in the alkane moiety; water-soluble salts of olefin sulfonates containing from about 12 to 24 carbon atoms; and β-alkyloxy alkane sulfonates containing from about 1 to 3 carbon atoms in the alkyl group and from about 8 to 20 carbon atoms in the alkane moiety.

Further exemplary useful as anionic surfactants are carboxylates such as alkyl carboxylates which include those which may be represented by the general formula:

R—COO-M+ wherein R is a straight or branched hydrocarbon chain containing from about 9 to 21 carbon atoms, and M is a metal or ammonium ion; polyalkoxycarboxylates, representative of which are polyethoxycarboxylates which may be represented by the general formula:

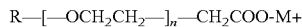

R—[—OCH$_2$CH$_2$—]$_n$—CH$_2$COO-M+ wherein R is a straight chained or branched hydrocarbon chain which may include an aryl moiety, but is desirably a straight chained or branched hydrocarbon chain; and n is an integer value of from 1-24.

In certain embodiments of the invention, one or more anionic surfactants are excluded from the self-adhesive lavatory treatment compositions of the invention.

Exemplary useful cationic surfactants include quaternary ammonium compounds and salts thereof which may include quaternary ammonium germicides characterized by the general structural formula:

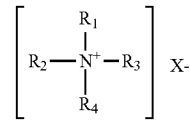

where at least one or $R_1$, $R_2$, $R_3$ and $R_4$ is a alkyl, aryl or alkylaryl substituent of from 6 to 26 carbon atoms, and desirably the entire cation portion of the molecule has a molecular weight of at least 165. The alkyl substituents may be long-chain alkyl, long-chain alkoxyaryl, long-chain alkylaryl, halogen-substituted long-chain alkylaryl, long-chain alkylphenoxyalkyl, arylalkyl, etc. The remaining substituents on the nitrogen atoms other than the abovementioned alkyl substituents are hydrocarbons usually containing no more than 12 carbon atoms. The substituents $R_1$, $R_2$, $R_3$ and $R_4$ may be straight-chained or may be branched, but are preferably straight-chained, and may include one or more amide, ether or ester linkages. The counterion X may be any salt-forming anion which permits water solubility of the quaternary ammonium complex. Exemplary counterions include halides, for example chloride, bromide or iodide, or methosulfate.

Exemplary quaternary ammonium salts within the above description include the alkyl ammonium halides such as cetyl trimethyl ammonium bromide, alkyl aryl ammonium halides such as octadecyl dimethyl benzyl ammonium bromide, N-alkyl pyridinium halides such as N-cetyl pyridinium bromide, and the like. Other suitable types of quaternary ammonium salts include those in which the molecule contains either amide, ether or ester linkages such as octyl phenoxy ethoxy ethyl dimethyl benzyl ammonium chloride, N-(laurylcocoaminoformylmethyl)-pyridinium chloride, and the like. Other very effective types of quaternary ammonium compounds which are useful as germicides include those in which the hydrophobic radical is characterized by a substituted aromatic nucleus as in the case of lauryloxyphenyltrimethyl ammonium chloride, cetylaminophenyltrimethyl ammonium methosulfate, dodecylphenyltrimethyl ammonium methosulfate, dodecylbenzyltrimethyl ammonium chloride, chlorinated dodecylbeuzyltrimethyl ammonium chloride, and the like.

Preferred quaternary ammonium compounds which act as germicides and which are be found useful in the practice of the present invention include those which have the structural formula:

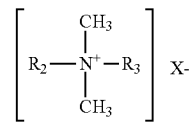

wherein $R_2$ and $R_3$ are the same or different $C_8$-$C_{12}$ alkyl, or $R_2$ is $C_{12-16}$ alkyl, $C_{8-18}$ alkylethoxy, $C_{8-18}$alkylphenolethoxy and $R_3$ is benzyl, and X is a halide, for example chloride, bromide or iodide, or methosulfate. The alkyl groups recited in $R_2$ and $R_3$ may be straight-chained or branched, but are preferably substantially linear. The counterion X is as described previously.

As further preferred quaternary ammonium comprising surfactant constituents are those presently commercially available in the Suga®Quat series of materials, which include at least those materials presently commercially available as: Suga®Quat L-1010, described as being laurdimoniumhydroxypropyl decylglucosides chloride; Suga®Quat L-1210, described as being laurdimoniumhydroxypropyl laurylglucosides chloride; Suga®Quat S-1010, described as being stearyldimoniumhydroxypropyl decylglucosides chloride; Suga®Quat S-1210, described as being stearyldimoniumhydroxypropyl laurylglucosides chloride; Suga®Quat S-1218, described as being stearyldimoniumhydroxypropyl laurylglucosides chloride; and Suga®Quat TM-8310, described as being cocoglucosides hydroxypropyltrimonium chloride. All of the foregoing are presently commercially available from ex. Colonial Chemical, Inc. (South Pittsburgh, Tenn. (USA)). Exemplary useful Suga®Quat series of materials include those as described in U.S. Pat. No. 6,881,710 (the contents of which are incorporated by reference), which are materials which conform to one or both of the following structures (a) and/or (b):

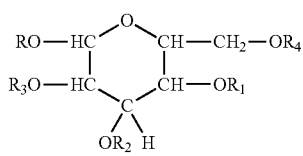

(a)

in which:
R is $C_8$-$C_{22}$ alkyl;
$R_1$, $R_2$, $R_3$ and $R_4$ are independently selected from the group consisting of: H, and the further group,

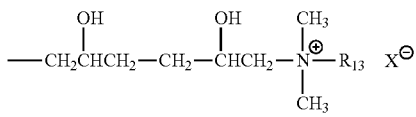

in which $R_{13}$ is $C_8$-$C_{22}$ alkyl with the proviso that $R_1$, $R_2$, $R_3$ and $R_4$ are not all H; and X is a halogen, preferably Cl, Br or I,

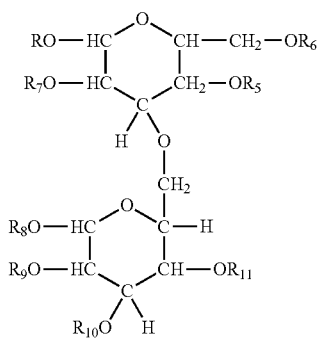

(b)

in which:
R is $C_8$-$C_{22}$ alkyl;
$R_5$, $R_6$, $R_7$ $R_8$, $R_9$, $R_{10}$ and $R_{11}$ are independently selected from the group consisting of: H, and the further group,

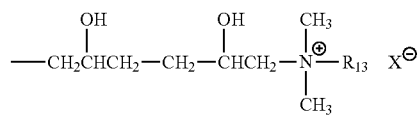

in which $R_{13}$ is $C_8$-$C_{22}$ alkyl, with the proviso that $R_5$, $R_6$, $R_7$, $R_8$, $R_9$, $R_{10}$ and $R_{11}$ are not all H:
and X is a halogen, preferably Cl, Br or I.

The foregoing materials according to structures (a) and/or (b) are generally provided as aqueous compositions comprising about 35% wt. of one or more of the said foregoing compounds according to formula (a) and/or (b) and the balance being substantially water.

Of the foregoing materials according to formula (a) or (b), particularly preferred are those which generally conform to the following structure:

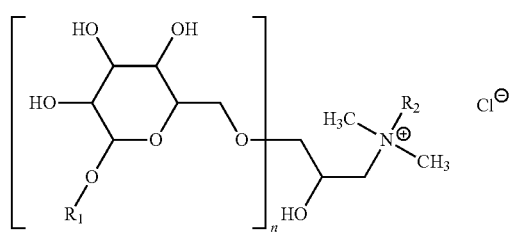

in which: n has a value of 1 or more, and $R_1$ and $R_2$ are carbon containing moieties.

A further preferred cationic surfactant is alkyl hydroxyethyl dimethyl ammonium chloride, commercially available as Praepagen® HEQ-10 (ex. Clariant).

In certain embodiments of the invention, one or more cationic surfactants are excluded from the self-adhesive lavatory treatment compositions of the invention.

In certain preferred embodiments of the invention, the detersive surfactant constituent comprises (or consists essentially of, or consists of) one or more cationic surfactants.

Exemplary useful nonionic surfactants, include known art nonionic surfactant compounds. Practically any hydrophobic compound having a carboxy, hydroxy, amido, or amino group with a free hydrogen attached to the nitrogen can be condensed with ethylene oxide or with the polyhydration product thereof, polyethylene glycol, to form a water soluble nonionic surfactant compound. Further, the length of the polyethylenoxy hydrophobic and hydrophilic elements may various. Exemplary nonionic compounds include the polyoxyethylene ethers of alkyl aromatic hydroxy compounds, e.g., alkylated polyoxyethylene phenols, polyoxyethylene ethers of long chain aliphatic alcohols, the polyoxyethylene ethers of hydrophobic propylene oxide polymers, and the higher alkyl amine oxides. Alkoxylated alkyl phenols including those commercially available under the tradename Triton® X series (Union Carbide Chem. Co., Danbury Conn.) may be advantageously added.

Further nonionic surfactants which may be optionally present in the inventive composition are alkyl polyglycoside. Suitable alkyl polyglycosides are known nonionic surfactants which are alkaline and electrolyte stable. Alkyl mono and polyglycosides are prepared generally by reacting a monosaccharide, or a compound hydrolyzable to a monosaccharide with an alcohol such as a fatty alcohol in an acid medium. Various glycoside and polyglycoside compounds including alkoxylated glycosides and processes for making them are disclosed in U.S. Pat. No. 2,974,134; U.S. Pat. No. 3,219,656; U.S. Pat. No. 3,598,865; U.S. Pat. No. 3,640,998; U.S. Pat. No. 3,707,535; U.S. Pat. No. 3,772,269; U.S. Pat. No. 3,839,318; U.S. Pat. No. 3,974,138; U.S. Pat. No. 4,223,129; and U.S. Pat. No. 4,528,106.

A preferred group of alkyl glycoside surfactants suitable for use in the practice of this invention may be represented by formula I below:

$$RO-(R_1O)_y-(G)_xZ_b \quad \text{I}$$

wherein:
R is a monovalent organic radical containing from about 6 to about 30, preferably from about 8 to about 18 carbon atoms;
$R_1$ is a divalent hydrocarbon radical containing from about 2 to about 4 carbon atoms;
O is an oxygen atom;
y is a number which has an average value from about 0 to about 1 and is preferably 0;
G is a moiety derived from a reducing saccharide containing 5 or 6 carbon atoms; and
x is a number having an average value from about 1 to 5 (preferably from 1.1 to 2);
Z is $O_2M^1$, $$-O-\overset{O}{\underset{\|}{C}}-R_2,$$

$O(CH_2)$, $CO_2M^1$, $OSO_3M^1$, or $O(CH_2)SO_3M^1$; $R_2$ is $(CH_2)CO_2M^1$ or $CH=CHCO_2M^1$; (with the proviso that Z can be $O_2M^1$ only if Z is in place of a primary hydroxyl group in which the primary hydroxyl-bearing carbon atom, —$CH_2OH$, is oxidized to form a $$-\overset{O}{\underset{\|}{C}}-OM^1$$

group);
b is a number of from 0 to 3x+1 preferably an average of from 0.5 to 2 per glycosal group;
p is 1 to 10,
$M^1$ is H or an organic or inorganic cation, such as, for example, an alkali metal, ammonium, monoethanolamine, or calcium.

As defined in Formula I above, R is generally the residue of a fatty alcohol having from about 8 to 30 and preferably 8 to 18 carbon atoms. Examples of such alkylglycosides as described above include, for example, APG™ 325 CS GLYCOSIDE which is described as being a 50% $C_9$-$C_{11}$ alkyl polyglycoside, also commonly referred to as D-glucopyranoside, (commercially available from Henkel Corp, Ambler Pa.) and GLUCOPON™ 625 CS which is described as being a 50% $C_{10}$-$C_{16}$ alkyl polyglycoside, also commonly referred to as a D-glucopyranoside.

A further class of exemplary useful nonionic surfactants include nonionic surfactant compounds which are based on a polymeric alkylene oxide block copolymer, Polymeric alkylene oxide block copolymers include nonionic surfactants in which the major portion of the molecule is made up of block polymeric $C_2$-$C_4$ alkylene oxides. Such nonionic surfactants, while preferably built up from an alkylene oxide chain starting group, and can have as a starting nucleus almost any active hydrogen containing group including, without limitation, amides, phenols, thiols and secondary alcohols. One preferred class of such nonionic surfactants containing the characteristic alkylene oxide blocks are those which may be generally represented by the formula (A):

$$HO-(EO)_x(PO)_y(EO)_z-H \quad (A)$$

where EO represents ethylene oxide,
PO represents propylene oxide,
y equals at least 15,
$(EO)_{x+z}$ equals 20 to 50% of the total weight of said compounds, and, the total molecular weight is preferably in the range of about 2000 to 15,000.

Examples of further and particularly useful nonionic surfactant compounds which include as a major portion of the molecule a block polymeric alkylene oxide block are those materials presently commercially available under the tradename "Pluronic®", and in particular the Pluronic® F series, Pluronic® L series, Pluronic® P series, as well as in the Pluronic® R series, each of which are generally described to be block copolymers of propylene oxide and ethylene oxide, and are presently commercially available from BASF AG (Ludwigshafen, Germany) as well as from BASF Corp. (Mt. Olive Township, N.J.).

In certain embodiments of the invention, one or more nonionic surfactants are excluded from the self-adhesive lavatory treatment compositions of the invention.

Exemplary useful albeit optional amphoteric surfactants include alkylbetaines, particularly those which may be represented by the following structural formula:

$$RN(CH_3)_2CH_2COO^-$$

wherein R is a straight or branched hydrocarbon chain which may include an aryl moiety, but is preferably a straight hydrocarbon chain containing from about 6 to 30 carbon atoms. Further exemplary useful amphoteric surfactants include amidoalkylbetaines, such as amidopropylbetaines which may be represented by the following structural formula:

$$RCONHCH_2CH_2CH_2N^+(CH_3)CH_2COO^-$$

wherein R is a straight or branched hydrocarbon chain which may include an aryl moiety, but is preferably a straight hydrocarbon chain containing from about 6 to 30 carbon atoms. Further useful amphoteric surfactants include sultaines, including compounds which may be represented by the following formula:

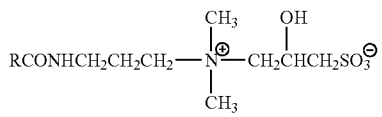

In the above formulae, R represents a $C_8$ to $C_{24}$ alkyl group, and is preferably a $C_{10}$ to $C_{16}$ alkyl group.

In certain embodiments of the invention, one or more amphoteric surfactants and/or zwitterionic surfactants are excluded from the self-adhesive lavatory treatment compositions of the invention.

Further exemplary useful optional surfactants include sarcosinate surfactants which are alkali metal salts of N-alkyl-N-acyl amino acids. These are salts derived from the reaction of (1) N-alkyl substituted amino acids of the formula:

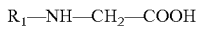

where $R_1$ is a linear or branched chain lower alkyl of from 1 to 4 carbon atoms, especially a methyl, for example, aminoacetic acids such as N-methylaminoacetic acid (i.e. N-methyl glycine or sarcosine), N-ethyl-aminoacetic acid, N-butylaminoacetic acid, etc., with (2) saturated natural or synthetic fatty acids having from 8 to 18 carbon atoms, especially from 10 to 14 carbon atoms, e.g. lauric acid, and the like.

The resultant reaction products are salts which may have the formula:

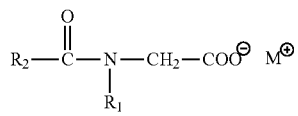

where M is an alkali metal ion such as sodium, potassium or lithium; $R_1$ is as defined above; and wherein $R_2$ represents a hydrocarbon chain, preferably a saturated hydrocarbon chain, having from 7 to 17 carbon atoms, especially 9 to 13 carbon atoms of the fatty acyl group

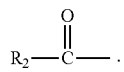

Exemplary useful sarcosinate surfactants include cocoyl sarcosinate, lauroyl sarcosinate, myristoyl sarcosinate, palmitoyl sarcosinate, stearoyl sarcosinate and oleoyl sarcosinate, and tallow sarcosinate. Such materials are also referred to as N-acyl sarcosinates.

In certain embodiments of the invention, one or more sarcosinate surfactants are excluded from the self-adhesive lavatory treatment compositions of the invention.

The surfactant constituent comprises from about 0.5% wt. to about 35% wt., preferably from about 5% wt. to about 25% wt. of the self-adhesive lavatory treatment compositions, based on the said compositions of which they form a part. Preferred surfactant compounds are ones which provide good foaming and cleaning characteristics to the self-adhesive lavatory treatment compositions described herein.

The identity of especially preferred surfactants and of the surfactant constituent of the self-adhesive lavatory treatment compositions of the invention are disclosed with reference to one or more of the example compositions.

Water is an essential constituent and comprises between about 25% wt. and 75% wt., preferably about 30% wt. and about 60% wt. of the self-adhesive lavatory treatment compositions of the invention. The water may be tap water, but is preferably distilled and is most preferably deionized water. If the water is tap water, it is preferably substantially free of any undesirable impurities such as organics or inorganics, especially minerals salts which are present in hard water which may thus undesirably interfere with the operation of the constituents present in the compositions according to the invention.

Preferably, the amount of water added to the compositions is advantageously sufficient to ensure that the resultant self-adhesive lavatory treatment compositions form self-supporting gels, which do not appreciably sag or run when formed. Preferably the self-adhesive lavatory compositions are "ringing gels". These ringing gels do not appreciably sag or run when formed, and are amorphous, non-crystalline materials which exhibit a ringing phenomena when they are excited by mechanical vibrations. Such ringing gels are believed to be microemulsion gels which are formed by the incorporation of the dispersed organic solvent constituent within the water, adhesion promoter constituent and the surfactant constituent which form the bulk of the self-adhesive lavatory treatment compositions of the invention.

In certain preferred embodiments the self-adhesive lavatory treatment compositions of the invention are ringing gels, which form within 48 hours of being mixed, preferably within 24 hours of being mixed.

The inventive compositions preferably and in some embodiments necessarily further comprise a co-adhesion promoter constituent based on one or more oxyalkylenated compounds. These oxyalkylenated compound(s) typically comprise ethylene oxide groups ("EO") (oxyethylenated compounds), or propylene oxide groups ("PO") (oxypropylenated compounds) or both ("EO/PO") (oxyethylenated/oxypropylenated compounds). Of course, a plurality of oxyalkylenated compound(s) may be used in the primary adhesion promoter constituent of the adhesive lavatory treatment compositions.

Exemplary suitable oxyalkylenated compounds may be selected from: polyethylene glycols, polyethylene glycol esters and/or polypropylene glycol esters, polyethylene glycol ethers and/or polypropylene glycol ethers, alkoxylated acyl derivatives, ethoxylated acyl polyol derivatives, oxyalkylenated (especially) oxyethylenated triesters of glycerol and of fatty acids, and mixtures thereof.

Non-limiting examples of suitable polyethylene glycols which may be used in the composition of the invention include ethylene oxide polycondensates having a number of ethylene oxide (EO) units of greater than 10, and preferably greater than about 20. The ethylene oxide number preferably range from about 10 to about 50,000 and preferably from about 20 to about 10,000. Non-limiting examples of such polyethylene glycols include polyethylene glycol comprising 7,000 EO (CTFA name: PEG-7M), polyethylene glycol comprising 75 EO (CTFA name: PEG-75), polyethylene glycol comprising 20,000 EO (CTFA name: PEG-20M), and polyethylene glycol comprising 150 EO (CTFA name: PEG-150).

Non-limiting examples of suitable polyethylene glycol esters and/or polypropylene glycol esters include condensates of polyethylene glycol and/or polypropylene glycol with one or more fatty acids. These compounds typically have the formula:

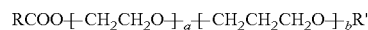

wherein:
each of R and R' independently represent: hydrogen or a saturated or unsaturated, linear or branched, hydroxylated or non-hydroxylated alkyl chain containing from 1 to 30 carbon atoms, preferably from 12 to 22 carbon atoms, or an aryl chain, with the proviso that R and R' are not simultaneously hydrogen,
a=0-300
b=300, and preferably a+b is greater than or equal to 10, preferably at least 20, still more preferably at least 30.

Non-limiting examples of polyethylene glycol acid esters and/or polypropylene glycol acid esters include polyethylene glycol distearate (150 EO), PEG-150 dibehenate, polyethylene glycol palmitostearate (120 EO), the copolymer of polyethylene glycol (30 EO) and of 12-hydroxystearic acid, and polyethylene glycol stearate (40 EO). Examples of compounds according to the foregoing formula wherein R and R' are both hydrogen, such compound may be polyoxyethylene polyoxypropylene copolymers.

Non-limiting examples of polyethylene glycol ethers and/or polypropylene glycol ethers include condensates of polyethylene glycol and/or polypropylene glycol with one or more fatty alcohols. These compounds typically conform to the formula:

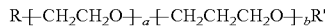

wherein:

each of R and R' represent, independently of each other, hydrogen or a saturated or unsaturated, linear or branched, hydroxylated or non-hydroxylated alkyl chain containing from 1 to 30 carbon atoms, preferably from 12 to 22 carbon atoms, or an aryl chain, with the proviso that R and R' are not simultaneously hydrogen.

a=0-300 b=0-300, and preferably a+b is greater than or equal to 10, preferably at least 20, still more preferably at least 30.

Non-limiting examples of such polyethylene glycol ethers include oxyethylenated (30 EO) cetyl alcohol, oxyethylenated (15 EO) oleyl alcohol, oxyethylenated (50 EO) oleyl alcohol, oxyethylenated (10 EO) behenyl alcohol, oxyethylenated (30 EO) behenyl alcohol, oxyethylenated (12 EO) lauryl alcohol, oxyethylenated (23 EO) lauryl alcohol, oxyethylenated (20 EO) 2-octyldodecyl alcohol, oxyethylenated (20 EO) isocetyl alcohol, oxyethylenated (10 EO) oleyl alcohol, oxyethylenated (20 EO) oleyl alcohol, oxyethylenated (100 EO) stearyl alcohol, and oxyethylenated (21 EO) stearyl alcohol.

Non-limiting examples of polyethylene glycol/polypropylene glycol ethers in particular, include oxyethylenated (5 EO) oxypropylenated (5 PO) lauryl alcohol, oxypropylenated (3 PO) myristyl alcohol, oxyethylenated (20 EO) oxypropylenated (5 PO) cetyl alcohol, oxyethylenated (26 EO) oxypropylenated (26 PO) butyl alcohol, oxyethylenated (26 EO) oxypropylenated (26 PO) butyl alcohol, oxyethylenated (30 EO) oxypropylenated (6 PO) decyltetradecanol, and oxyethylenated (25 EO) oxypropylenated (25 PO) lauryl alcohol.

Non-limiting examples of ethoxylated alkyl or aryl derivatives of polyol include oxyethylenated derivatives of fatty acid esters or of fatty alcohol ethers and of a polyol such as glycerol, sorbitol, glucose or pentaerythritol. Suitable derivatives of this type include, for example, oxyethylenated (78 EO) glyceryl cocoate, oxyethylenated (120 EO) methylglucose dioleate, oxyethylenated (40 EO) sorbitan septaoleate, oxyethylenated (10 EO) polyglyceryl (2 mol of glycerol) laurate, oxyethylenated (60 EO) glyceryl isostearate, oxyethylenated (20 EO) glyceryl monostearate, oxyethylenated (200 EO) glyceryl stearate, and oxyethylenated (150 EO) pentaerythrityl tetrastearate, such as the product sold under the name Crothix™ (ex. Croda, Inc.)

Non-limiting examples of suitable oxyalkylenated glyceryl triesters of fatty acids include, for example, oxyethylenated (6 EO) caprylic/capric acid glycerides, and oxyethylenated (50 EO) olive oil.

Particularly preferred for use in the co-adhesion promoter constituent are compounds according to the structure:

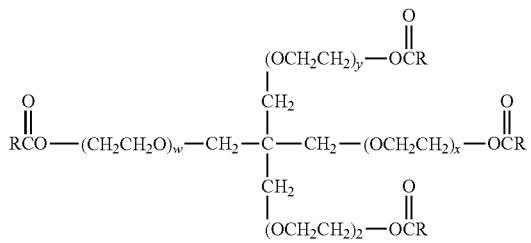

wherein,

R is a fatty acid moiety, preferably a stearic fatty acid moiety, and the sum of w+x+y+z is in the range of 50-1500, preferably in the range of 70-500, more preferably in the range of about 100-350 and especially preferably about 150.

A particularly preferred primary adhesion promoter constituent is a material presently commercially available under the tradename Crothix (ex. Croda, Inc.).

Further particularly preferred co-adhesion promoters include high molecular weight water-soluble poly(ethylene oxide) polymers, which desirably have molecular weights (weight average) in the range from about 100,000 to about 8,000,000. Such high molecular weight water-soluble poly(ethylene oxide) polymers are presently commercially available as Polyox resins (ex. Dow Chem. Co.).

In certain embodiments, the co-adhesion promoter constituent is pasty or is solid at room temperature (20° C.).

Mixtures of two or more of the foregoing materials and/or compounds may be used to provide the co-adhesion promoter constituent. Alternatively a single of the foregoing materials and/or compounds can be used to provide the co-adhesion promoter constituent.

In certain preferred embodiments, one or more of the foregoing co-adhesion promoters are expressly excluded from the adhesive lavatory treatment compositions.

In further preferred embodiments a co-adhesion promoter is necessarily present in the adhesive lavatory treatment compositions.

When present, the co-adhesion promoter constituent comprises from about 0.001% wt.-5% wt., preferably about 0.05% wt.-2.5% wt. based on the total weight of the inventive composition of which it forms a part.

In embodiments of the invention, wherein both a primary adhesion promoter and a co-adhesion promoter are concurrently present, preferably the weight ratio of the former to the latter is at least about not more than 10:1, and especially preferably is not more than about 20:1

The identity of especially preferred co-adhesion promoter constituents and their content within self-adhesive lavatory treatment compositions of the invention are disclosed with reference to one or more of the Example compositions.

Optionally the self-adhesive lavatory treatment compositions of the invention may comprise one or more further optional constituents which may impart a further aesthetic or technical benefit to the said self-adhesive lavatory treatment compositions. When present, such further optional constituents are generally present in a cumulative amount of less than about 25% wt. based on the total weight of the self-adhesive lavatory treatment compositions wherein one or more such further optional constituents may be present. By way of non-limiting example such further optional constituents include one or more of coloring agents, fragrances and fragrance solubilizers, viscosity modifying agents, thickeners, bleaches, bleach releasing compounds, oxidizing agents, germicidal agents, pH adjusting agents and pH buffers including organic and inorganic salts as well as organic and inorganic acids, builders, chelating agents, opacifying agents, titanium dioxide, inert inorganic or organic fillers, visually discernible additive materials, hydrotropes, enzymes as well as other biologically active constituents, anti-oxidants, preservatives, and anti-corrosion agents, as well as other optional constituents known to the skilled artisan. When one or more of the optional constituents is added, i.e., fragrance and/or coloring agents, the esthetic and consumer appeal of the product is often favorably improved. The use and selection of these optional constituents should be based on imparting a desired additional aesthetic or technical benefit, as well as to ensure compatibility with the further constituents present in the inventive sell-adhesive lavatory treatment compositions, especially such that the desirable self-adhesive properties of the self-adhesive lavatory treatment compositions are not deleteriously diminished.

Optionally the inventive compositions may further comprise a germicide constituent (other than cationic germicidally active quaternary ammonium halide surfactants noted above) which has germicidal or antimicrobial efficacy against at least one of gram-positive or gram-negative pathogens, e.g., bacteria or other microorganisms. Such may be based, for example, on one or more non-cationic antimicrobial compounds or constituents, e.g., halophenols such 3-trifluoromethyl-4,4'-dichlorocarbanilide, 3,3',4-trichlorocarbanilide, as well as 2,4-dichloro-3,5-m-xylenol ("DCMX"). The phenol based non-cationic antimicrobials are preferred, of which parachlorometacresol ("PCMC") and especially parachlorometaxylenol ("PCMX").

Alternately such may be based, for example, on one or more phenol derivatives such as those based on 2-hydroxydiphenyl compounds, including Triclosan® (ex. Ciba), those based on 2,2'-hydroxy-5,5'-dibromo-diphenyl ethers, such as one or more of chlorophenols (o-,m-,p-), 2,4-dichlorophenol, p-nitrophenol, picric acid, xylenol, p-chloro-m-xylenol, cresols (o-,m-,p-), p-chloro-m-cresol, pyrocatechol, resorcinol, 4-n-hexylresorcinol, pyrogallol, phloroglucin, carvacrol, thy mol, p-chlorothymol, o-phenylphenol, o-benzylphenol, p-chloro-o-benzylphenol, phenol, 4-ethylphenol, and 4-phenolsulfonic acid, as well as further diphenol compounds such as hexachlorophene, tetrachlorophene, dichlorophene, 2,3-dihydroxy-5,5'-dichlorodiphenyl sulfide, 2,2'-dihydroxy-3,3',5,5'-tetrachlorodiphenyl sulfide, 2,2'-dihydroxy-3,5',5,5',6,6'-hexachlorodiphenyl sulfide, and 3,3'-dibromo-5,5'-dichloro-2,2'-dihydroxydiphenylamine, and especially "Triclocarban", 3,4,4'-trichlorocarbanilide as well as derivatives thererof.

The optional germicide constituent may also be based on one or more acids, including organic acids such as salicylic and citric acid, and/or inorganic acid such as hydrochloric acid when present in effective amounts in order to sufficiently acidify the treatment composition formed from the inventive compositions.

Optionally the inventive compositions may comprise a preservative constituent. Such preservatives are primarily included to reduce the growth of undesired microorganisms within the composition during storage prior to use. Exemplary useful preservatives include compositions which include parabens, including methyl parabens and ethyl parabens, glutaraldehyde, formaldehyde, 2-bromo-2-nitropropoane-1,3-diol, 5-chloro-2-methyl-4-isothiazolin-3-one, 2-methyl-4-isothiazoline-3-one, and mixtures thereof. One exemplary composition is a combination 5-chloro-2-methyl-4-isothiazolin-3-one and 2-methyl-4-isothiazolin-3-one where the amount of either component may be present in the mixture anywhere from 0.001 to 99.99 weight percent, based on the total amount of the preservative. Further exemplary useful preservatives include those which are commercially including a mixture of 5-chloro-2-methyl-4-isothiazolin-3-one and 2-methyl-4-isothiazolin-3-one marketed under the trademark KACTHON® CG/ICP as a preservative composition presently commercially available from Rohm and Haas (Philadelphia, Pa.). Further useful and commercially available preservative compositions include KATHON® CG/ICP II, a further preservative composition presently commercially available from Rohm and Haas (Philadelphia, Pa.), PROXEL® which is presently commercially available from Zeneca Biocides (Wilmington, Del.), SUTTOCIDE® A which is presently commercially available from Sutton Laboratories (Chatam, N.J.) as well as TEXTAMER® 38AD which is presently commercially available from Calgon Corp. (Pittsburgh, Pa.). An exemplary and preferred preservative is 1,3-bis(hydroxymethyl)5,5-dimethylimidazolidine-2,4-dione, which is presently conmmercially available as NIPAGARD® DMDM from Clariant Corp. This product, as supplied, is described to comprise 1,3-bis(hydroxymethyl)5,5-dimethylimidazolidine-2,4-dione, 44-46% wt. water, 17-19% wt. formaldehyde and not more than 1% of other unspecified materials. When present this may be included in effective amounts, and advantageously when present to one or more preservative compositions of preparations are present amounts of from about 0.001-1% wt. Based on the weight treatment composition which it forms a part.

Optionally the inventive compositions may comprise bleaches and/or bleach releasing compounds. Examples of such bleaches and/or bleach releasing compounds include those selected from the group of the alkali metal and alkaline earth salts of hypohalite, haloamines, haloimines, haloimides and haloamides. All of these are believed to produce hypohalous bleaching species in situ. Hypochlorite and compounds producing hypochlorite in aqueous solution are preferred, although hypobromite is also suitable. Representative hypochlorite-producing compounds include sodium, potassium, lithium and calcium hypochlorite, chlorinated trisodium phosphate dodecahydrate, potassium and sodium dichloroisocyanurate and trichlorocyanuric acid. Organic bleach sources suitable for use include heterocyclic N-bromo and N-chloro imides such as trichlorocyanuric and tribromocyanuric acid, dibromo- and dichlorocyanuric acid, and potassium and sodium salts thereof; N-brominated and N-chlorinated succinimide, malonimide, phthalimide and naphthalimide. Also suitable are hydantoins, such as dibromo- and dichloro dimethylhydantoin, chlorobromodimethyl hydantoin. N-chlorosulfamide (haloamide) and chloramine (haloamine). Particularly preferred is sodium hypochlorite having the chemical formula NaOCl Optionally an oxidizing constituent or agent may be present in the inventive compositions. Examples of such an oxidizing agent include peroxyhydrates or other agent which releases hydrogen peroxide in aqueous solution. Such materials are per se, known to the art. Peroxyhydrates are to be understood as including hydrogen peroxide as well as any material or compound which in an aqueous composition yields hydrogen peroxide. Non-limiting examples of such materials and compounds include: alkali metal peroxides including sodium peroxide and potassium peroxide, alkali perborate monohydrates, alkali metal perborate tetrahydrates, alkali metal persulfate, alkali metal percarbonates, alkali metal peroxyhydrate, alkali metal peroxydihydrates, and alkali metal carbonates especially where such alkali metals are sodium or potassium. Further useful are various peroxydihydrate, and organic peroxyhydrates such as urea peroxide. Desirably, when present, the oxidizing agent is hydrogen peroxide.

When an oxidizing agent is present, minor amounts (<1% wt.) of one or more known art hydrogen peroxide stabilizers such as one or more organic phosphonates, stannates, pyrophosphates, as well as citric acid, may also be present.

Optionally, the inventive compositions may include one or more coloring agents, which are used to impart a desirable visual appearance, e.g., color(s) to the compositions. One or more known art pigments and dyes may be advantageously included in certain embodiments and may be added in effective amounts, which, when present, are advantageously included in an amount of from about 0.00001-2% wt. Such coloring agents may be provided in an aqueous carrier, in an organic solvent carrier or a mixture thereof.

Optionally, the inventive compositions include a fragrance constituent, which may comprises one or more fragrance materials. Fragrance materials may generally be divided into three main groups: (1) the essential oils and products isolated from these oils; (2) products of animal origin; and (3) synthetic chemicals.

The essential oils consist of complex mixtures of volatile liquid and solid chemicals found in various parts of plants. Mention may be made of oils found in flowers, e.g., jasmine, rose, mimosa, and orange blossom; flowers and leaves, e.g., lavender and rosemary; leaves and stems, e.g., geranium, patchouli, and petitgrain; barks, e.g., cinnamon; woods, e.g., sandalwood and rosewood; roots, e.g., angelica; rhizomes, e.g., ginger; fruits, e.g., orange, lemon, and bergamot; seeds, e.g., aniseed and nutmeg; and resinous exudations, e.g., myrrh. These essential oils consist of a complex mixture of chemicals, the major portion thereof being terpenes, including hydrocarbons of the formula $(C_5H_8)_n$ and their oxygenated derivatives. Hydrocarbons such as these give rise to a large number of oxygenated derivatives, e.g., alcohols and their esters, aldehydes and ketones. Some of the more important of these are geraniol, citronellol and terpineol, citral and citronellal, and camphor. Other constituents include aliphatic aldehydes and also aromatic compounds including phenols such as eugenol. In some instances, specific compounds may be isolated from the essential oils, usually by distillation in a commercially pure state, for example, geraniol and citronellal from citronella oil: citral from lemon-grass oil; eugenol from clove oil; linalool from rosewood oil; and safrole from sassafras oil. The natural isolates may also be chemically modified as in the case of citronellal to hydroxy citronellal, citral to ionone, eugenol to vanillin, linalool to linalyl acetate, and safrol to heliotropin.

Animal products used in perfumes include musk, ambergris, civet and castoreum, and are generally provided as alcoholic tinctures.

The synthetic chemicals include not only the synthetically made, but also naturally occurring isolates mentioned above, and such may include their derivatives and compounds unknown in nature, e.g., isoamylsalicylate, amylcinnamic aldehyde, cyclamen aldehyde, heliotropin, ionone, phenylethyl alcohol, terpineol, undecalactone, and gamma nonyl lactone.

Fragrance materials as received from a supplier may be provided as an aqueous or organically solvated composition, and may include as a hydrotrope or emulsifier a surface-active agent, typically a surfactant, in minor amount, and such are frequently proprietary blends of one or more of the foregoing materials. Such fragrance materials may be suitably used as fragrance constituents.

When included in the inventive compositions the fragrance constituent may be included in any effective amount which provides a desired olfactory benefit. Such olfactory benefit may be to impart a fragrance and benefit, to provide an odor masking benefit, or even to providing odor neutralization benefit. Advantageously, fragrance constituent comprises between about 0.01-7.5% wt. of the inventive compositions in which they form a part.

Optionally the inventive composition may include visibly discernible materials which may, for example, be particles or particulates which are visibly discernible to a consumer, particularly by a consumer having normal "20/20" vision, visually inspecting a mass or dose of the self-adhesive lavatory treatment compositions applied to a hard surface. Non-limiting examples of such visibly discernible materials include materials which provide a visual effect of suspended inclusions within the mass of a self-adhesive lavatory treatment compositions which may be advantageous from a consumer standpoint. Such visibly discernible materials may for example be particulates of mica, colored beads such as glass beads or beads, comminuted particles or spheres formed from uncolored or colored synthetic polymers, visible light reflective particles (commonly referred to as "glitter") which are typically formed of comminuted metallized or reflective polymer particles, alginate beads such as those described in PCT/US95/08313, U.S. Pat. No. 7,196, 046, U.S. Pat. No. 7,291,586 B2, as well as other visibly discernible materials known to the art which would provide a similar function. Preferably such visibly discernible materials have a maximum dimension in the range of from about 100 to about 1000 μm.

Optionally the inventive compositions may include one or more inert inorganic or inert organic fillers compounds or materials which are preferably insoluble in water or in organic solvents. Non-limiting examples of such inert fillers include powders such as silicates, chalk, talc, kaolin, chemically modified magnesium aluminum silicate, hydrated aluminum silicate, fumed silica, and mixtures thereof.

Optionally the inventive compositions may include one or more constituents which function as viscosity modifying agents or thickeners. Non-limiting examples of such materials include polysaccharide polymers especially those selected from cellulose, alkyl celluloses, alkoxy celluloses, hydroxy alkyl celluloses, alkyl hydroxy alkyl celluloses, carboxy alkyl celluloses, carboxy alkyl hydroxy alkyl celluloses, naturally occurring polysaccharide polymers such as xanthan gum, guar gum, locust bean gum, tragacanth gum, or derivatives thereof. Further constituents which function as viscosity modifying agents or thickeners include polycarboxylate polymers, polyacrylamides, clays, and mixtures thereof.

Non-limiting examples of useful cellulose derivatives include methyl cellulose ethyl cellulose, hydroxymethyl cellulose hydroxy ethyl cellulose, hydroxy propyl cellulose, carboxy methyl cellulose, carboxy methyl hydroxyethyl cellulose, hydroxypropyl cellulose, hydroxy propyl methyl cellulose, ethylhydroxymethyl cellulose and ethyl hydroxy ethyl cellulose.

Non-limiting examples of useful polycarboxylate polymers are those have a molecular weight from about 500,000 to about 4,000,000, preferably from about 1,000,000 to about 4,000,000, with, preferably, from about 0.5% to about 4% crosslinking. Preferred polycarboxylate polymers include polyacrylate polymers including those sold under trade names Carbopol®, Acrysol® ICS-1 and Sokalan®. The preferred polymers are polyacrylates. Other monomers besides acrylic acid can be used to form these polymers including such monomers as ethylene and propylene which act as diluents, and maleic anhydride which acts as a source of additional carboxylic groups.

Non-limiting examples of further useful polycarboxylic acid polymer compositions which can be employed include, for example, crosslinked copolymers of acrylates, (meth) acrylic acid, maleic anhydride, and various combinations thereof.

Non-limiting examples of useful clay thickeners include colloid-forming clays, for example, such as smectite and or attapulgite types. The clay materials can be described as expandable layered clays, i.e., aluminosilicates and magnesium silicates. The term "expandable" as used to describe the instant clays relates to the ability of the layered clay structure to be swollen, or expanded, on contact with water. The expandable clays used herein are those materials classified geologically as smectites (or montmorillonite) and attapulgites (or polygorskites). Commercially available clays include, for example, montmorillonite, bentonite, volchonskoite, nontronite, beidellite, hectorite, saponite, sauconite and vermiculite. The clays herein are available under various trade names such as Gelwhite GP, Gelwhite H, Mineral Colloid BP, and Laponite from Southern Clay Products, Inc., Texas; and Van Gel O from R. T. Vanderbilt.

Further constituents which may be optionally included include one or more of: inorganic filler materials, such as one or more of silica, fumed silica, silica dioxide, carbon black, comminuted polymer beads or particulates, sodium silicate. Further materials based on rosins, tall oil and/or terpene compounds may also be included, e.g., polyterpenic resins (e.g., Dercolyte LTG, ex. DRT), or rosin esters, such as diethylene glycol rosin esters (e.g., Dertoline DEG 2, ex. DRT); certain of such may be useful in the organic solvent constituent. Exemplary chelating agents include alkali metal, ammonium and substituted ammonium polyacetates, carboxylates, polycarboxylates and polyhydroxysulfonates, as well as tetra sodium salt of glutamic acid-N,N-diacetic acid, as well as methyl-glycine-diacetic acid. Nonlimiting examples of commercially available chelating agents include those marketed under the "Dissolvine" trademark (ex. AkzoNobel) including Dissolvine GL-PD-S, and Dissolvine E-CA-10 materials. Further useful as an optional constituent are butane homopolymers, e.g., polyisobutene, such as may be commercially obtained as TPC 1350 from Texas Petro Chemicals Co. Further useful as an optional constituent is an emulsifying agent, preferably sucrose acetate isobutyrate such as is commercially available as Eastman SAIB-100 (ex. Eastman Chemical Co.)

Other optional constituents, although not specifically elucidated above, may also be considered useful for inclusion in the inventive compositions particularly wherein such impart a further aesthetic or technical benefit to the said self-adhesive lavatory treatment compositions.

The compositions of the invention may be formed combining the constituents, and mixing them in a suitable vessel, for example a laboratory beaker to which is provided a stirrer, preferably a propeller or paddle type store mounted on a shaft driven by an electric motor, and preferably also wherein the laboratory beaker is mounted upon a hotplate or other heating source in order to allow variation in the control of the temperature between about room temperature (approx. 20° C.) and about 100° C. Such temperature control facilitates the formation of the compositions wherein one or more the constituents may have a melting point above room temperature. Advantageously the compositions of invention are formed by first producing a first pre-mixture is formed by blending the adhesion promoter based on a fatty alcohol polyglycol ether, the organic solvent constituent, the at least one surfactant, and when present any co-adhesion promoter constituents. Such blending may be achieved by suitably mixing the foregoing constituents at a suitable temperature within the foregoing range (20° C.-100° C.) for sufficient time in order to ensure that a homogenous mixture is formed. Typically, depending upon the volume of the mixing vessel and the characteristics of the stirrer a homogenous mixture is formed, suitably such occurs between 5 min.-120 min. of stirring. If necessary, the composition may be allowed to cool (if it was raised to an elevated temperature) in order to allow for the introduction of further constituents, e.g., one or more optional constituents such as fragrances, colorants, etc., which are preferably added to the homogenous mixture, at a temperature suitable for their addition. For example, were fragrances are contemplated to be use, advantageously the temperature of the homogenous mixture is sufficiently low to avoid the premature flashing off of one or more the fragrance compounds prior to being blended. Advantageously, such further constituents are first formed into a second pre-mixture in a separate vessel, with a separate stirrer, at a suitable temperature, e.g. room temperature (approx. 20° C.) and about 100° C. as stirring continues, typically for between 5-120 min. until the second pre-mixture is homogenous. Thereafter, measured amounts of the second pre-mixture may be added, under stirring conditions, to the first pre-mixture as suitable temperature in order to form a homogenous blend from the first, and second pre-mixtures. Subsequently a measured amount of water, which may optionally include any further remaining constituents not already provided in the first premixture and/or the second premixture, which water is preferably at a temperature of between about 10-50° C., is added to this resultant homogenous blend. It is been observed that that upon addition of the water, even under reduced stirring conditions that the onset of the formation of the gel is swift and with some formulations nearly instantaneous, sometimes forming on the order of between 0.1-15 seconds, preferably between about 0.5-10 seconds as the water (with any remaining constituents) is combined to the balance of the constituents of the homogenous mixture formed from the first and second pre-mixtures. Advantageously, the resultant gel is allowed to rest in undisturbed state for a number of hours thereafter, preferably for least about 24 hours to allow for the "setting" of the resultant gel.

The addition of the water to the balance of the constituents of the homogenous mixture may take place in a suitable container. For example, the water may be added to the beaker containing the quantity of the homogenous mixture but advantageously, in certain embodiments, an aliquot of the homogenous mixtures provided either concurrently, or serially with a measured aliquots of water directly into a cavity of a dispensing device, such as is hereafter described or referred to. Such allows for simplified process for the manufacture of one or more dispensing devices containing a quantity of the self-adhesive lavatory treatment composition, e.g., as blisters, dispensing devices which expel a quantity of the composition, pouches, etc., as is hereinafter described more fully as dispensers or dispensing means.

Preferred self-adhesive lavatory treatment compositions of the invention are viscous or pasty, and may be characterized in having a viscosity in the range of from about 150,000 cP to about 7,000,000 cP, but preferably from about 200,000 to about 5,000,000. The viscosity may be determined utilizing conventional analytical instruments.

The compositions of the invention may be applied directly to hard surfaces, which may be vertical, or sloped, and may be applied to and retained thereupon even on dry surfaces. As previously noted, especially preferred hard surfaces include water wetted or dry surfaces of lavatory appliances, particularly the interior surface of a toilet bowl. Once applied, the compositions may be flushed away after a plurality of flushing operations, preferably following a relatively large number of flushing operations. While it is naturally understood that the operating parameters of lavatory devices, e.g., toilets, vary considerably and that the range of compositions which are taught herein are also variable, preferably, once applied a mass (preferably between about 2 and about 10 grams, more preferably from about 3 to about 7 grams, and covering a surface area of approximately about 1 to about 10 $cm^2$) of the inventive composition are retained in the hard surface for at least 5, and in order of increasing preference, at least 10, 15, 20, 25, 30, 35, 40, 45, 50, 55, 60, 60, 65, 70, 75 and 80 flushes, or until the mass of the of the self-adhesive lavatory treatment compositions is eroded by the flushing water of the lavatory device.

The compositions of the invention may be applied either directly by a consumer, but are more conveniently applied utilizing a dispensing means which contains a quantity of the self-adhesive lavatory treatment composition as taught herein. For example, a larger quantity of an the self-adhesive lavatory treatment compositions may be provided in a dispenser such as compressible tube, or bottle, compressible piston and syringe type dispenser, compressible bag or blister-type formed package which is compressed by a consumer to expel and dispense a quantity of the self-adhesive lavatory treatment composition onto a hard surface. After the self-adhesive lavatory treatment composition is delivered from the dispensing device onto a surface, (e.g, by extrusion, or otherwise being expelled) the dispensing device is removed from the part of the lavatory appliance and prior to the use of the self-adhesive lavatory treatment composition to treat the lavatory appliance, viz., the formation of a lavatory treatment liquid by contacting the dispensed self-adhesive lavatory treatment composition with water from the lavatory appliance, e.g. flush water. Thus, once the self-adhesive lavatory treatment composition is dispensed onto a part of a lavatory appliance (or other hard surface) it is removed and may be discarded or refilled as may be desired. Once removed, the dispensing device thus plays no further role in the treatment of the lavatory appliance. The amount dispensed per dispensing operation may be variable, or may be predetermined, so that an approximately uniform mass/quantity of the self-adhesive lavatory treatment composition may be applied as a dose to a hard surface. The self-adhesive lavatory treatment compositions may be supplied in a suitable dispenser which dispenses a single dose of the compositions during an application step or application operation. Such dispensing means may be, for example, prefilled cartridges such as blisters, dispensing devices such as may comprise a plurality of cartridges each of which contains a single unit dose, which is expelled from the device, piston containing cylindrical dispensers which may include means to limit the travel of the piston through the bore of the cylindrical dispenser so that upon displacement of the piston, a dose of the self-adhesive lavatory treatment composition is expelled. The self-adhesive lavatory treatment compositions may be supplied in a suitable dispenser which dispenses/expels a plurality of single doses of the self-adhesive lavatory treatment composition as well. Further suitable dispensing means are a pouch which contains in its interior a mass of the self-adhesive lavatory treatment composition; in application the pouch may be opened at one end thereof and the self-adhesive lavatory treatment composition squeezed out onto a hard surface, or one part of the pouch may be peeled away, e.g., a film, and thereafter the exposed self-adhesive lavatory treatment composition may be applied to a hard surface by a consumer, and thereafter the remaining part of the pouch may be withdrawn and discarded by a consumer. Certain particularly preferred dispensing means include those disclosed in pending patent applications GB patent application 1007066.2, or GB patent application 1007064.7, or in U.S. Design patent application U.S. Ser. No. 29/383660 or in U.S. D651,489 the contents of each of which are herein incorporated by reference, or the self-adhesive lavatory treatment composition may be supplied in a suitable dispenser which dispenses a plurality of single doses.

Figure 2:
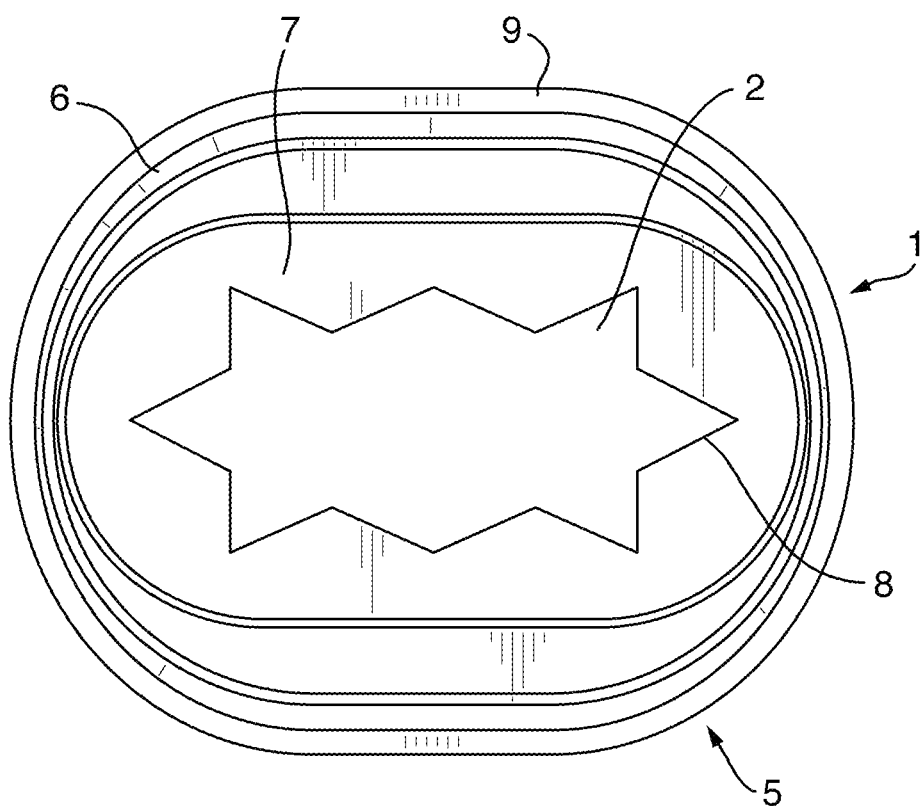
FIG. 2 depicts a bottom view of the preferred dispenser.

With reference to FIGS. 1 and 2, a preferred example of a dispensing means is depicted; FIG. 1 provides a perspective view, and FIG. 2 provides a plan view of the underside or base of a dispenser 1. A slideable piston plate 2 affixed to a handle 3 is present within a bore 4 of the base 5 of the dispenser 1. At an end of the bore 4 is present a peripheral skirt 6 which forms part of the base 5 which extends beyond a base plate 7 which spans the bore 4 just prior to the skirt 6. It is understood that when the handle 3 is used to pull the piston plate 2 in a direction away from the base plate 7, such defines an interior cavity within the bore 4, and defined by the bore 4, the base plate 7 and the piston plate 2. The base plate 7 further includes an orifice 8, here a 16 sided polygon. Such provides an illustrative embodiment only, as virtually any other geometric shape may be used to define the orifice, or plurality of orifices which may be present within the base plate 7. Conversely when the piston plate 2 is moved or urged towards the base plate 7, any self-adhesive lavatory treatment composition present within the interior cavity is expelled or extruded out from the internal cavity through the orifice 8. When the base margin 9 of the skirt 6 is placed in contact with an generally planar, or slightly curved surface (e.g., the curves surface of the interior of a lavatory appliance, e.g., a toilet bowl) such establishes a gap or distance between the base plate 7 and the said surface. In use a consumer grips the handle 3, places the margin 9 of the skirt 6 on a hard surface and compresses the piston plate 2 to expel the self-adhesive lavatory treatment composition out from the dispenser 1 where it adhered. The provision of the polygonal orifice provides a decorative pattern to the mass or the self-adhesive lavatory treatment composition adhered to the hard surface. Thereafter the consumer withdraws the device 1 from the lavatory appliance. Other dispensing means which provide a similar function as described above or otherwise may be used to contain and dispense a quantity or mass of the self-adhesive lavatory treatment compositions taught herein may also be used.

Such a dispenser containing a self-adhesive lavatory treatment composition as described herein may be a vendible product, and represents a further aspect of the present invention.

Compositions of self-adhesive lavatory treatment compositions according to the invention are particularly well adapted for use with a lavatory appliance in order to provide a cleaning and/or fragrancing and/or sanitizing and/or other technical benefit thereto. In use, a quantity of an self-adhesive lavatory treatment composition is applied directly to a part of a lavatory appliance, advantageously in a part thereof wherein the adhered self-adhesive lavatory treatment composition is in the path of flowing water, e.g., flush water, which impinges upon the adhered self-adhesive lavatory treatment compositions and slowly erodes the same, and thereby forming a lavatory treatment liquid which comprises the water which entrains one or more of the constituents of the self-adhesive lavatory treatment compositions which has been released by the water. Depending upon the specific constituents used to form the self-adhesive lavatory treatment compositions, various technical benefits may be provided by the thus formed lavatory treatment liquid. Thus, an aspect of the invention provides a method of for treating a lavatory appliance comprising the steps of applying an self-adhesive lavatory treatment composition directly to a part of a lavatory appliance wherein the adhered self-adhesive lavatory treatment composition is in the path of flowing water, e.g., flush water, which impinges upon the adhered self-adhesive lavatory treatment compositions and slowly erodes the same, and, operating the lavatory appliance to dispense a flow of water which impinges on the self-adhesive lavatory treatment composition is in the path of flowing water thereby forming a lavatory treatment liquid which treats the lavatory appliance.

EXAMPLES

Example compositions of self-adhesive lavatory treatment compositions according to the invention were produced, and are identified on Table 1. The compositions disclosed on Table 1 demonstrate compositions according to the invention, including certain preferred embodiments of the invention. In these compositions, the constituents were used "as supplied" from their respective suppliers. The constituents constituted may have constitute less than 100% wt. "actives", or may have been supplied as constituting 100% wt. "active" of the named compound, as indicated in the following Tables 1 and Table 2. The identified amounts of each constituent on Table 1 are in "% wt." based on the total weight of a composition of which it forms a part. To each of the compositions, deionized water was added in "quantum sufficient" ("q.s.") in order to provide to 100% wt. of each composition.

The example compositions disclosed as E1-E12 were formed generally in accordance with the following steps:

To a laboratory beaker resting upon a variable temperature controllable hotplate, which laboratory beaker was further equipped with a electrically driven stirrer was provided measured amounts of the constituents of the "Part A" premixture (e.g. Genapol® O 200, anionic surfactant, parts of the organic solvent constituent), and the temperature of the contents of the beaker was raised to and regulated to 80° C.-85° C., and stirring continued under these conditions until a homogenous mixture was formed. Stirring took approximately 10-20 minutes, after which, the temperature of this homogenous, first pre-mixture was allowed to reduced to approximately to 60° C.-65° C.

While the first pre-mixture was being formed, into a separate lavatory beaker resting upon a variable temperature controllable hotplate and equipped with a further electrically driven stirrer were provided measured amounts of the "Part B" constituents (part of the organic solvent constituent, and where present, fragrance and/or coloring agent) were supplied and stirring was initiated while the temperature of the contents of this further beaker was maintained at a suitable temperature, advantageously between about 10-60° C. Stirring of the contents of the second laboratory beaker continued until homogenous which formed the second pre-mixture. Thereafter, the second beaker was removed, and its contents were added, under stirring conditions at a temperature of between about 60° C.-65° C. to form a resultant homogenous mixture. Stirring continued for approximately 5-15 minutes. Thereafter, the stirrer was removed, and to the laboratory beaker was added a measured aliquot of the deionized water ("Part C") which is approximately room temperature and a manual stirring rod or paddle was used. It was observed that the onset of gelling within this laboratory beaker was nearly instantaneous, and the formation of a firm gel had begun in as little as 5-10 seconds after the introduction of the water. Subsequently, the manual stirring rod or paddle was removed, and set aside. The contents of the laboratory beaker was allowed to rest, overnight (approx. 12 hours) at room temperature, on a laboratory tabletop, in order to allow for the gel to fully set.

Alternately where it was desired to form a self-adhesive lavatory treatment compositions directly within a dispensing device, (e.g, as depicted in U.S. D651,489) measured amounts of the combined first and second premixtures ("Part A" and "Part B") were added to a measured amount of water ("Part C") which was already present within the cavity or other receptacle of the dispenser, and following addition of the combined first and second premixtures, the contents of the dispenser were thus stirred, to form a homogenous mixture. Again, it was observed that the onset of gelling within the dispenser was nearly instantaneous, and the formation of a firm gel had begun in as little as 5-10 seconds after the introduction of the combined first and second premixtures to the water.

The lavatory treatment compositions according to E13-E25 of Table 1 were produced in accordance with the following general protocol. The first premix identified as Part A of Table 1 was formed by adding to a clean container (e.g., an open mouthed laboratory beaker) the adhesion promoter constituent based on a fatty alcohol polyglycol ether. The container was positioned in a combination laboratory hotplate and magnetic stirrer apparatus. The container was next heated from room temperature (approx. 20° C.), and at approx. 45° C. a magnetic stirring bar was introduced and stirring initiated, and continued until the adhesion promoter constituent reached approx. 80-90° C. to ensure the full melting of the adhesion promoter constituent had occurred. Thereafter under stirring conditions were added the remaining constituents of Part A, and stirring an heating was maintained until the contents of the container was homogenous, after which the heat source was deactivated or removed, and under continued stirring the contents of the container were allowed to cool, to 45° C.-65° C. During this time the second premix identified as Part B of Table 1 was formed in a similar manner, by mixing the constituents in a clean container, under stirring and under heating to a more moderate temperature of to approximately 55° C.-65° C., thus providing a homogenous mixture of the Part B constituents. Next, a measured amount of water, identified as Part C of Table 1, which was preferably distilled or deionized water, was heated to approx. 80° C. in a third container. When the water was sufficiently heated, the homogenous mixture of the first container and the second containers were combined, and optionally mixed, and thereafter this mixture was poured into the water of the third container and optionally mixed using a manual stirrer rod, or by a mechanical mixing means. The third container was briefly heated (approx. 2 minutes) at a low power setting (approx. 300 Watts) in a consumer grade microwave device, and thereafter was poured into one or more wide-bore syringes, and allowed to rest in a quiescent state for at least 5 minutes in order to allow for the initiation of hardening and formation of a self-supporting gel. Subsequently the lavatory treatment composition was dispensed from the syringe using a mechanical press to extrude the gelled lavatory treatment compositions into a small dispensing container which contained between 3-9 grams of the gelled lavatory treatment compositions.

Alternately following mixing of Part A, Part B and Part C, the resultant lavatory treatment composition may be allowed to rest in a quiescent state at room temperature until a self-supporting gel was formed. It is observed that when the resultant mixture was provided, e.g. poured, into small form, cavity, mold or container (e.g., having a volume of less than about 100 cc, the spontaneous formation of the self-supporting gel, preferably a ringing gel, occurs at a much faster rate then were the resultant mixture is allowed to rest at room temperature in a larger form, cavity, mold or container. The resultant gel may be ejected from the form, cavity, mold or container in which it had formed, and used as a lavatory treatment composition. Alternately the resultant gel may be heated, e.g, in a microwave, until it returns to a fluid form after which it can be poured again into a form, cavity, mold or container, or other process equipment, such as a nozzle or syringe from which the lavatory treatment composition may be dispensed.

Exemplary self-adhesive lavatory treatment compositions according to the invention are disclosed on the following Table 1.

TABLE 1

| | | E1 | E2 | E3 | E4 | E5 | E6 | E7 |
|---|---|---|---|---|---|---|---|---|
| Part A | Genapol ® O 200 | 30 | 28 | 26 | 30 | 30 | 30 | 20 |
| | sodium lauryl ether sulfate, 3EO (70%) | 18 | 18 | 14 | 18 | 18 | 18 | 14 |
| | PEG 4000 | — | — | — | — | — | — | — |
| | mineral oil (light) | 0.5 | 0.5 | 0.5 | 0.5 | 0.5 | 0.5 | 10 |
| | glycerin | 0.5 | | 0.5 | 0.5 | 0.5 | 0.5 | 0.5 |
| | propylene glycol | 3.0 | 3.0 | 2.0 | 5.0 | 5.0 | 5.0 | 7.0 |
| Part B | propylene glycol | 2.0 | — | 5.0 | — | 3.0 | 3.0 | — |
| | fragrance #1 | 3.0 | — | — | — | — | — | — |
| | fragrance #2 | — | 4.0 | 4.0 | — | — | — | — |
| | colorant #1 | — | 0.004125 | 0.004125 | — | — | — | — |
| | colorant #2 | — | 0.002000 | 0.002000 | — | — | — | — |
| | (propylene glycol from colorants #1, #2) | — | 0.606375 | 0.606375 | — | — | — | — |
| Part C | water (supplied to q.s.) | 43.0 | 45.8 | 47.3 | 46.0 | 43.0 | 43.0 | 57.5 |
| | TOTAL (% wt.): | 100 | 100 | 100 | 100 | 100 | 100 | 100 |
| | total % wt. propylene glycol from Part A and Part B | 5.00 | 3.60 | 7.60 | 5.00 | 8.00 | 8.00 | 7.00 |
| | ratio (%wt.) of propylene glycol:other organic solvents | 5:1 | 7.212:1 | 7.60:1 | 5:1 | 8:1 | 8:1 | 4.66:1 |
| | ratio (% wt.) of propylene glycol:mineral oil | 10:1 | 7.2:1 | 15.2:1 | 10:1 | 16:1 | 16:1 | 7:1 |
| | ratio (% wt.) of water:organic solvents | 10.75 | 13.11 | 15.79 | 7.66 | 7.16 | 7.16 | 6.76 |
| | ratio (%wt.) of water:propylene glycol and mineral oil | 12.28 | 13.11 | 18.95 | 8.36 | 7.81 | 7.81 | 7.18 |
| | ratio (% wt.) of water:propylene glycol | 14.33 | 15.29 | 23.69 | 9.2 | 8.6 | 8.6 | 8.2 |
| | onset of ringing gel properties (in hours) after initial formation of gel | 48+ | 48 | 24 | 24 | 24 | 24 | 12 to 18 |
| | lifespan (flush) testing (days) | NA | NA | 45+ | NA | NA | NA | NA |

| | | E8 | E9 | E10 | E11 | E12 |
|---|---|---|---|---|---|---|
| Part A | Genapol ® O 200 | 25 | 25 | 5 | 25 | 5 |
| | Genapol ® U 300 | — | 5 | 25 | — | 25 |
| | Praepagen HEQ (50%) | 5 | 5 | 5 | — | 5 |
| | Crothix PA | — | — | — | — | 1 |
| | mineral oil (light) | 2 | 2 | 2 | 4 | 2 |
| | glycerin | 8 | 8 | 8 | 8 | — |
| Part B | fragrance #1 | 4 | 4 | 4 | 4 | 4 |
| | colorant #1 | 0.001 | 0.001 | 0.001 | 0.001 | 0.001 |
| Part C | betaine surfactant (30%) | — | — | — | 25 | — |
| | water (supplied to q.s.) | 55.99 | 50.99 | 50.99 | 33.99 | 49.99 |
| | TOTAL (% wt): | 100 | 100 | 100 | 100 | 100 |
| | lifespan (flush) testing (days) | NA | NA | >7 days | NA | NA |

| | | E13 | E14 | E15 | E16 | E17 | E18 | E19 |
|---|---|---|---|---|---|---|---|---|
| Part A | Genapol ® O 200 | 25 | — | 5 | 25 | 22 | 30 | 25 |
| | Genapof ® U 300 | 5 | 25 | 25 | — | 6 | — | 5 |
| | Praepagen HEQ (50%) | 5 | 5 | 5 | 5 | 5 | 5 | — |
| | Sugaquat L1010 (35%) | — | — | — | — | — | — | 5 |
| | mineral oil (light) | 2 | 2 | 2 | 2 | 1.5 | 1.5 | 2 |
| | glycerin | 8 | 8 | 8 | 8 | 8 | 8 | 8 |
| Part B | fragrance #1 | 4 | 4 | 4 | 4 | 4 | 4 | 4 |
| | colorant #1 | 0.001 | 0.001 | 0.001 | 0.001 | 0.001 | 0.001 | 0.001 |
| Part C | preservative | 0.2 | 0.2 | 0.2 | 0.2 | 0.2 | 0.2 | 0.2 |
| | water (supplied to q.s.) | 503799 | 55.799 | 50.799 | 55.799 | 53.299 | 51.299 | 55.799 |
| | TOTAL (% wt.): | 100 | 100 | 100 | 100 | 100 | 100 | 100 |
| | application force (Kg) | 2.7 | 1.5 | 2.7 | 2.2 | 27 | 2.7 | 1.9 |
| | Foam | 7 | 7 | 7 | 7 | 8 | 8 | 7 |
| | lifespan (12 flushes/day) (days) | >7 | >7 | >7 | >7 | >7 | >7 | >7 |

TABLE 1-continued

|  |  | E20 | E21 | E22 | E23 | E24 | E25 |
|---|---|---|---|---|---|---|---|
| Part A | Genapol ® O 200 | 25 | — | 25 | — | — | 5 |
|  | Genapol ® U 300 | 5 | 25 | — | 40 | 50 | 40 |
|  | Praepagen HEQ (50%) | — | — | — | 5 | 5 | 5 |
|  | Sugaquat L1010 (35%) | 5 | 5 | 5 | — | — | — |
|  | mineral oil (light) | 2 | 2 | 2 | 2.5 | 2.5 | 2 |
|  | glycerin | 8 | 8 | 8 | 8 | 8 | 8 |
| Part B | fragrance #1 | 4 | 4 | 4 | 4 | 4 | 4 |
|  | colorant #1 | 0.001 | 0.001 | 0.001 | 0.001 | 0.001 | 0.001 |
| Part C | preservative | 0.2 | 0.2 | 0.2 | 0.2 | 0.2 | 0.2 |
|  | water (supplied to q.s.) | 55.798 | 60.799 | 60.799 | 40.299 | 30.299 | 35.799 |
|  | TOTAL (% wt.): | 100 | 100 | 100 | 100 | 100 | 100 |
|  | application force (Kg) | 1.7 | 1.3 | 1.3 | NA | NA | NA |
|  | Foam | 8 | 8 | 8 | 9 | 9 | 9 |
|  | lifespan (12 flushes/day) (days) | >7 | >7 | >7 | >10 | >10 | >10 |

The identity of the constituents of Table 1 are disclosed on the following Table 2. As noted, unless otherwise indicated the constituents were provided as "100% wt. actives".

TABLE 2

| Genapol ® O 200 | oleyl alcohol polyglycol ether, 20 mols (avg) ethoxylation, (100% wt. actives) (ex. Clariant) |
|---|---|
| Genapol ® U 300 or Genapol ® O 300 | oleyl alcohol polyglycol ether, 30 mols (avg) ethoxylation, (100% wt. actives) (ex. Clariant) |
| sodium lauryl ether sulfate, 3EO (70%) | sodium lauryl ether sulfate, 3 mols (avg) ethoxylation, (ex. Rokita) (70% wt. actives) |
| PEG 4000 | polyethylene glycol, (weight average) M.W. 4000, (100% wt. actives) (ex. BASF) |
| Praepagen HEQ | alkyl hydroxyethyl dimethyl ammonium chloride (50% wt. actives) (ex. Clariant) |
| betaine surfactant (30%) | betaine surfactant, supplied as AMPHOTENSID B4 (ex. Zschimmer & Schwartz Italiana S.p.A) (30% wt. actives) |
| Suga-quat L1010 (35%) | stearyldimoniumhydroxypropyl decylglucosides chloride, chloride salt (35% wt. actives) (ex. Colonial Chemical) |
| mineral oil (light) | technical grade light mineral oil (100% actives) (organic solvent) |
| glycerine | technical grade light mineral oil (100% actives) (organic solvent) |
| propylene glycol | technical grade supplied as (100% actives) (ex. DOW Chem. Co.) (organic solvent) |
| fragrance #1 | proprietary fragrance material |
| fragrance #2 | proprietary fragrance material |
| colorant #1 | pigment/dye (1 part pigment/dye dispersed in 99 parts of propylene glycol) |
| colorant #2 | pigment/dye (1 part pigment/dye dispersed in 99 parts of propylene glycol) |
| preservative | 1,3-dimethoyl-5,5-dimethyl hydantoin, (35-39% actives) supplied as Nipagard DMDMH |
| water | deionized water, supplied in 'quantum sufficient' (100% wt. actives) |

Samples of the compositions of the invention which were formed as described above formed "ringing gels" which were self-supporting, viz., and did not sag or run under their own weight.

The foregoing compositions E1-E7 demonstrate a first series of preferred embodiments of the inventive composition which include an anionic surfactant as an essential constituent, while the compositions of E8-E12 demonstrate compositions which do not include or require an anionic surfactant. Foregoing compositions E13-E25 demonstrate further preferred embodiments which were subjected to additional testing, including lifespan, adhesion and foam characteristics.

Measured aliquots of the composition according to E3 were applied to the interior of a toilet bowl on the curved interior sidewall and beneath the rim of the toilet bowl. Those which were not tested are labeled as "NA" as "not applicable". After multiple flushings of the toilet bowl, the composition according to E3 exhibited good and continued adhesivity to the sidewall. A good fragrance benefit and good foaming benefit were noted by the tester evaluating the performance of the composition.

Measured aliquots of the example compositions according to E13-E22 were applied to the interior of a toilet bowl on the curved interior sidewall and beneath the rim of the toilet bowl. These aliquots were applied utilizing a dispensing device as depicted in U.S. D651,489. Those which were not tested are labeled as "NA" as "not applicable". The flushing of the toilets followed the following sequence: The bowls were pre-set to flush every 2 hours, resulting in 12 flushes per 24 hours or 1 day. The 5 gram test supplied to the cavity of the dispensing device were evaluated based on duration of product left on the bowl wall through the predetermined flushing cycles and on a minimum success criteria of 1 week longevity or a lifespan of 7 days. Thereafter the testing ceased; regardless if any of the applied lavatory treatment composition was still present on the interior of the toilet bowl: the results of this test are reported on the foregoing Table 1. As indicated thereon, at least a part of the composition according to E13 through E22 was retained and visible on the sidewall of the toilet bowl following the 7 days to which the compositions were subjected to flushing testing. Similarly, at least a part of the composition according to E23 through E25 was retained and visible on the sidewall of the toilet bowl following the 10 days to which the compositions were subjected to flushing testing. During the testing, these compositions according to E13-E25 were all visually observed to exhibit good production of foam in the toilet bowl, and to exhibit good delivery of the fragrance to the toilet bowl.

The compositions of E13-E25 were additionally subjected to foam testing. The test was performed according to the following steps: The 5 g test samples of the lavatory treatment composition were supplied to the cavity of the applicator according to U.S. D651,489 (depicted on FIG. 1, and FIG. 2) and thereafter dispensed therefrom, and directly placed on the bowl sidewall of "Ideal Standard" toilets. After several flushes the foam quality and quantity was determined based on visual examination by a skilled observer of the foam present in the toilet bowl immediately after a flush cycle using the following scale:

| Rating: | Definition: |
|---|---|
| 10 | thick foam fully covering the entire surface of the water at the base of the toilet bowl |
| 8 | foam fully covering the entire surface of the water at the base of the toilet bowl |
| 5 | foam covering about ½ of the surface of the water at the base of the toilet bowl |
| 3 | crescent shaped foam at the edges of the base of the toilet bowl, covering some of the surface of the water at the base of the toilet bowl |
| 0 | no visible foam on surface of the water at the base of the toilet bowl. |

The results of this test are reported on Table 1.

The compositions of E13-E22 were additionally subjected to 'application force testing. The test was performed according to the following steps, which utilized a "TA.XT Plus" Texture Analyzer apparatus (ex. Texture Technologies, 18 Fairview Road, Scarsdale, N.Y. (US)). Pursuant to the test a 5 gram sample of each of the indicated tested formulations were provided to the cavity of the applicator depicted on FIG. 1, in which the piston part was withdrawn from the base part in order to define an internal cavity into which the aliquot of the composition was provided via a large bore syringe. The testing, and the aliquots of the example compositions were all at room temperature (approx. 20° C.). For each example composition tested, the same protocol was carried out. The handle of each piston part of the dispenser was firmly affixed to the downward probe of the Texture Analyzer apparatus, and on the testing plat or was provided a cleaned, glazed white ceramic bathroom tile with the white glazed surface essentially perpendicular to the base of the dispenser. The base plate of the applicator was initially spaced 1 inch (2.54 cm) above the top surface of the tile. The Texture Analyzer was preprogrammed to operate according to the following parameters: Test Mode=Compression, Pre-Test Speed=1.5 mm/second, Test Speed=1.5 mm/sec. Post-Test Speed 2.0 mm/sec, Target Mode=Distance, Travel Distance=19 mm, Strain=10%, Trigger Type=Pre Travel and Trigger Force=1.0 g–Auto. Using the foregoing device and settings, each tested composition was evaluated for the amount of force required to apply the gel of the composition to the ceramic tile surface, and the resulting force required (in kilograms) as determined by the Texture Analyzer apparatus is reported on Table 1. For the particular configuration of the particular dispenser, a dispensing force of about 2-4 kg was consider "consumer acceptable", while a great dispensing force of about 5 kg or greater was considered "consumer adverse."

The invention claimed is:

1. A self-adhesive lavatory treatment composition which comprises:

up to 50% wt. of an adhesion promoter constituent based on a fatty alcohol polyglycol ether as may be represented by the following structural formula (I):

within which,

R is an $C_{12}$-$C_{24}$ aliphatic mono- or poly-alkene moiety and which includes at least one unsaturation in the moiety, and n has a value of from 1 to 50;

1-25% wt. of an organic solvent constituent, which is liquid at room temperature (20° C.);

at least 25% wt. of water;

0.5-25% wt of a detersive cationic surfactant constituent according to structure (a) and/or structure (b):

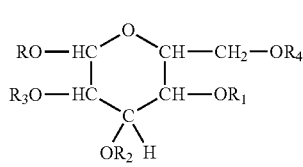

in which:

R is $C_8$-$C_{22}$ alkyl;

$R_1$, $R_2$, $R_3$ and $R_4$ are independently selected from the group consisting of: H, and the further group,

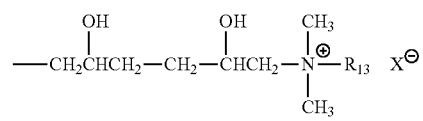

in which $R_{13}$ is $C_8$-$C_{22}$ alkyl with the proviso that $R_1$, $R_2$, $R_3$ and $R_4$ are not all H;

and X is a halogen,

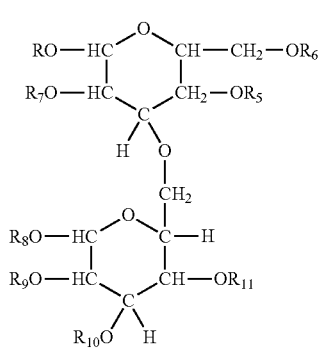

in which:

R is $C_8$-$C_{22}$ alkyl;

$R_5$, $R_6$, $R_7$, $R_8$, $R_9$, $R_{10}$ and $R_{11}$ are independently selected from the group consisting of: H, and the further group,

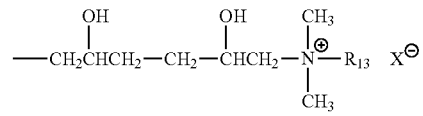

in which $R_{13}$ is $C_8$-$C_{22}$ alkyl, with the proviso that $R_5$, $R_6$, $R_7$, $R_8$, $R_9$, $R_{10}$ and $R_{11}$ are not all H;

and X is a halogen;

optionally a co-adhesion promoter constituent;

wherein in use, the said self-adhesive lavatory treatment compositions may be applied and adhered to a dry or wetted ceramic surface, especially the interior sidewall in a toilet bowl or other lavatory appliance, and wherein the said self-adhesive lavatory treatment compositions is retained adhered to the said surface following a plurality of flushes of water impinging upon the adhered self-adhesive lavatory treatment compositions.

2. A self-adhesive lavatory treatment composition according to claim 1, wherein in the fatty alcohol polyglycol ether of formula (I), wherein R is monounsaturated.

3. A self-adhesive lavatory treatment composition according to claim 1, wherein the said composition is a ringing gel.

4. A dispensing device, which comprises a quantity or mass of the self-adhesive lavatory treatment composition according to claim 1.

5. A self-adhesive lavatory treatment composition according to claim 1, wherein the organic solvent constituent comprises a polyhydroxy organic solvent and at least one other organic solvent.

6. A self-adhesive lavatory treatment composition according to claim 5, wherein:
   (a) the ratio (in % wt.) of polyhydroxy organic solvent: other solvents of the organic solvent constituent is in the range of about 4-12:1; and/or
   (b) the ratio (in % wt.) of polyhydroxy organic solvent: mineral oil is in the range of about 5-20:1; and/or
   (c) the ratios (in % wt.) of water:organic solvent constituent is in the range of about 5-20:1 and/or
   (d) the ratios (in % wt.) of water:polyhydroxy organic solvent constituent is in the range of about 5-25:1.

7. A dispensing device which comprises a quantity of a self-adhesive lavatory treatment composition according to claim 1, which dispensing device is adapted to extrude a quantity of the self-adhesive lavatory treatment composition onto a lavatory appliance, and which dispensing device is adapted to be removed prior to formation of a lavatory treatment liquid.

8. A method for treating a lavatory appliance comprising the steps of:
   applying a self-adhesive lavatory treatment composition according to claim 1 directly to a part of a lavatory appliance wherein the adhered self-adhesive lavatory treatment composition is in the path of flowing water, which impinges upon the adhered self-adhesive lavatory treatment compositions and slowly erodes the same, and,
   operating the lavatory appliance to dispense a flow of water which impinges on the self-adhesive lavatory treatment composition is in the path of flowing water thereby forming a lavatory treatment liquid which treats the lavatory appliance.

9. A self-adhesive lavatory treatment composition according to claim 1 which consists essentially of:
   up to 50% wt. of an adhesion promoter constituent based on a fatty alcohol polyglycol ether as may be represented by the following structural formula (I):

within which, R is an $C_{12}$-$C_{24}$ aliphatic mono- or polyalkene moiety, and n has a value of from 1 to 50 and, which include at least one unsaturation in the moiety;
   1-25% wt. of an organic solvent constituent, which is liquid at room temperature (20° C.);
   0.5-25% wt. of a detersive cationic surfactant constituent constituent according to structure (a) and/or structure (b):

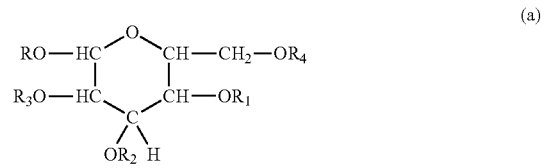

in which:
R is $C_8$-$C_{22}$ alkyl;
$R_1$, $R_2$, $R_3$ and $R_4$ are independently selected from the group consisting of: H, and the further group,

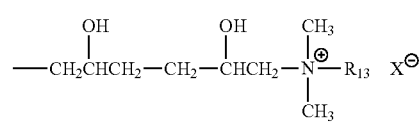

in which $R_{13}$ is $C_8$-$C_{22}$ alkyl with the proviso that $R_1$, $R_2$, $R_3$ and $R_4$ are not all H;
and X is a halogen,

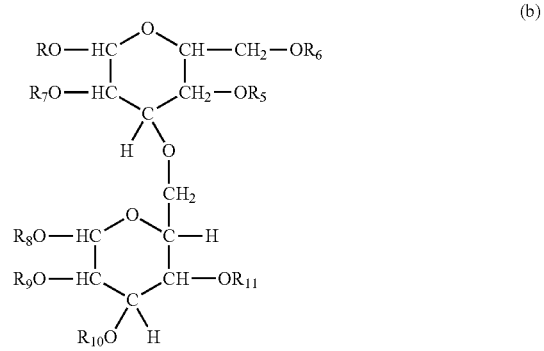

in which:
R is $C_8$-$C_{22}$ alkyl;
$R_5$, $R_6$, $R_7$, $R_8$, $R_9$, $R_{10}$ and $R_{11}$ independently from the group consisting of: H, and the further group,

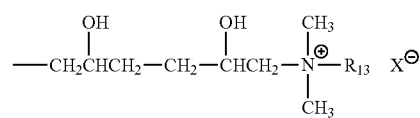

in which $R_{13}$ is $C_8$-$C_{22}$ alkyl, with the proviso that $R_5$, $R_6$, $R_7$, $R_8$, $R_9$, $R_{10}$ and $R_{11}$ are not all H;
and X is a halogen;
   to 100% wt. of water;
   optionally a co-adhesion promoter constituent, preferably based on one or more oxyalkylenated compounds;
   wherein in use, the said self-adhesive lavatory treatment compositions may be applied and adhered to a dry or wetted ceramic surface, especially the interior sidewall in a toilet bowl or other lavatory appliance, and wherein the said self-adhesive lavatory treatment compositions is retained adhered to the said surface following a plurality of flushes of water impinging upon the adhered self-adhesive lavatory treatment compositions.

10. A self-adhesive lavatory treatment composition according to claim 1, which comprises a co-adhesion promoter constituent based on one or more oxyalkylenated compounds.

11. A self-adhesive lavatory treatment composition according to claim 6 wherein:
   (a) the ratio (in % wt.) of polyhydroxy organic solvent: other solvents of the organic solvent constituent is in the range of about 4.5-10:1; and/or
   (b) the ratio (in % wt.) of polyhydroxy organic solvent: mineral oil is in the range of about 7:18:1; and/or
   (c) the ratios (in % wt.) of water:organic solvent constituent is in the range of about 6-16:1; and/or
   (d) the ratios (in % wt.) of water:polyhydroxy organic solvent constituent is in the range of about 7-25:1.

12. A self-adhesive lavatory treatment composition according to claim 6, wherein at least two of (a), (b), (c) and (d) are satisfied.

13. A self-adhesive lavatory treatment composition according to claim 12, wherein at least three of (a), (b), (c) and (d) are satisfied.

14. A self-adhesive lavatory treatment composition according to claim 12, wherein at all four of (a), (b), (c) and (d) are satisfied.

15. A self-adhesive lavatory treatment composition according to claim 1, which comprises about 25% wt. to about 75% wt. of water.

16. A dispensing device which comprises a quantity of a self-adhesive lavatory treatment composition according to claim 15, which dispensing device is adapted to extrude a quantity of the self-adhesive lavatory treatment composition onto a lavatory appliance, and which dispensing device is adapted to be removed prior to formation of a lavatory treatment liquid.

17. A method for treating a lavatory appliance comprising the steps of:
   applying a self-adhesive lavatory treatment composition according to claim 15 directly to a part of a lavatory appliance wherein the adhered self-adhesive lavatory treatment composition is in the path of flowing water, which impinges upon the adhered self-adhesive lavatory treatment compositions and slowly erodes the same, and,
   operating the lavatory appliance to dispense a flow of water which impinges on the self-adhesive lavatory treatment composition is in the path of flowing water thereby forming a lavatory treatment liquid which treats the lavatory appliance.

* * * * *